(12) United States Patent
DiMaio et al.

(10) Patent No.: US 8,606,344 B2
(45) Date of Patent: Dec. 10, 2013

(54) INTEGRATED PATIENT BED SYSTEM

(75) Inventors: John Michael DiMaio, Dallas, TX (US);
James Watson, Plano, TX (US); Jose Melendez, Lakeway, TX (US); Roma Moza, Plano, TX (US); Harry Tibbals, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 536 days.

(21) Appl. No.: 12/433,597

(22) Filed: Apr. 30, 2009

(65) Prior Publication Data
US 2009/0275808 A1 Nov. 5, 2009

Related U.S. Application Data

(60) Provisional application No. 61/049,243, filed on Apr. 30, 2008, provisional application No. 61/146,223, filed on Jan. 21, 2009.

(51) Int. Cl.
*A61B 5/00* (2006.01)
(52) U.S. Cl.
USPC ........... 600/407; 600/306; 600/473; 600/476; 5/601
(58) Field of Classification Search
USPC ......... 600/407, 425, 427, 430, 473, 476, 300; 5/600, 601, 940; 340/573.1
See application file for complete search history.

(56) References Cited

U.S. PATENT DOCUMENTS

| | | | |
|---|---|---|---|
| 4,991,585 A * | 2/1991 | Mawhinney | 600/430 |
| 5,853,005 A * | 12/1998 | Scanlon | 600/459 |
| 6,205,354 B1 | 3/2001 | Gellermann et al. | |
| 6,287,253 B1 | 9/2001 | Ortega et al. | |
| 6,351,573 B1 | 2/2002 | Schneider | |
| 7,155,273 B2 * | 12/2006 | Taylor | 600/476 |
| 2002/0016533 A1 | 2/2002 | Marchitto et al. | |
| 2003/0159219 A1 | 8/2003 | Harrison et al. | |

(Continued)

FOREIGN PATENT DOCUMENTS

| | | |
|---|---|---|
| KR | 10-0690205 B1 | 3/2007 |
| WO | 0078217 A1 | 12/2000 |
| WO | 2007020643 A2 | 2/2007 |
| WO | 2007144810 A1 | 12/2007 |

OTHER PUBLICATIONS

International Search Report and Written Opinion for PCT/US2009/042440 dated Jun. 28, 2010.

(Continued)

*Primary Examiner* — Unsu Jung
*Assistant Examiner* — Phong K Huynh
(74) *Attorney, Agent, or Firm* — Edwin S. Flores; Chalker Flores, LLP

(57) ABSTRACT

The present invention includes an integrated system and methods for patient treatment, the system includes a hospital bed; a plurality of patient diagnostic and treatment devices connected to a network, wherein each of the devices can communicate to a network and exchange information with the network about the care of a patient; and a processor accessible adjacent to the bed and connected to the network to integrate information obtained from the devices through the network with one or more additional sources of information databases, wherein the processor can communicate to one or more patient treatment devices either directly or via the network and the processor directs the one or more patient treatment devices to change the treatment of the patient.

21 Claims, 20 Drawing Sheets

(56) References Cited

U.S. PATENT DOCUMENTS

| | | | |
|---|---|---|---|
| 2005/0124864 A1* | 6/2005 | Mack et al. | 600/300 |
| 2006/0152378 A1* | 7/2006 | Lokhorst et al. | 340/666 |
| 2006/0278240 A1 | 12/2006 | Spillman, Jr. et al. | |
| 2007/0073156 A1 | 3/2007 | Zilberman et al. | |
| 2008/0060138 A1 | 3/2008 | Price et al. | |
| 2009/0163819 A1 | 6/2009 | De Kok et al. | |

OTHER PUBLICATIONS

International Search Report and Written Opinion for PCT/US2009/042436 dated Dec. 23, 2009.
Bennett, et al., "Paraplegic Pressure Sore Frequency Versus Circulation measurements," Journal of Rehabilitation Research and Development, vol. 27, No. 2, (1990), 14 pages.
Allen, John, "Photoplethysmography and its Application in Clinical Physiological Measurement," Physiol. Meas., (2007), 28:R1-R39.
Bello, Ysabel M., et al., "Recent Advances in Wound Healing," JAMA, Feb. 9, 2000, vol. 283, No. 6, pp. 716-718.
Binzoni, T., et al., "Detectioon Limits of Multi-Spectral Optical Imaging Under the Skin Surface," Phys. Med. Biol., (2008), 53:617-636.
Humphreys, K., et al., "A CMOS Camera-Based Pulse Oximetry Imaging System," Proceedings of the 2005 IEEE Engineering in Medicine and Biology 27th Annual Conference, Shanghai, China, Sep. 1-4, 2005, pp. 3494-3497.
Humphreys, Kenneth, et al., "Noncontact Simultaneoud Dual Wavelength Photoplethysmography: A Further Step Toward Noncontact Pulse Oximetry," Review of Scienfitic Instruments, (2007), 78:044304-1-044304-6.
Kerekes, John, et al., "Spectral Imaging of Skin: Experimental Observations and Analyses," Proceedings of SPIE vol., (2006), 6142, pp. 61423V-1-61423V-,8.
Leonardi, Lorenzo, et al., "Evaluating the Health of Compromised Tissues Using a Near Infrared Spectroscopic Imaging System in Clinical Settings: Lessons Learned," Proceedings of SPIE, (2003), vol. 4959, pp. 89-99.
Mansfield, James R., et al., "Tissue Viability by Multispectral Near Infrared Imaging: A Fuzzy C-Means Clustering Analysis," IEEE Transactions on Medical Imaging, Dec. 1998, vol. 17, No. 6, pp. 1011-1018.
Palero, J.A., et al., "In Vivo Nonlinerar Spectral Imaging in Mouse Skin," Optics Express, May 15, 2006, vol. 14, No. 10, 8 pages.
Payette, Jeri R., et al., "Assessment of Skin Flaps Unsing Optically Based Methods for Measuring Blood Flow and Oxygenation," Plast. Reconstr. Surg., (2005), 115:539-546.
Shannon, Claude E., "Communication in the Presence of Noise," Proceedings of the IRE, Jan. 1949, vol. 37, No. 1, pp. 10-21.
Stamatas, Georgios N., et al., "In Vivo Monitoring of Cutaneous Edema Using Spectral Imaging in the Visible and Near Infrared," Journal of Investigative Dermatology, (2006), 126, pp. 1753-1760.
Texas Instruments, "TMS320DM6437 Digital Media Processor Data Sheet," Nov. 2006, 305 pages.
Wieringa, FP., et al., In Vitro Demonstration of an Sp02-Camera, Computers in Cardiology, (2007), 34:749-751.
Hauben, Daniel Joseph, et al., "On the History of the Free Skin Graft," Annals of Plastic Surgery, Sep. 1982, vol. 9, No. 3, pp. 242-246.
Jones, Robert H., et al., "Coronary Bypass Surgery with or without Surgical Ventri1717.cular Reconstruction," The New England Journal of Medicine, Apr. 23, 2009, vol. 360, No. 17, pp. 1705-1717.
Wieringa, F. P., et al., "Contactless Multiple Wavelength Photoplethysmographic Imaging: A First Step Toward "SpO2 Camera" Technology," Annals of Biomedical Engineering, Aug. 2005, vol. 33, No. 8, pp. 1034-1041.
Leachtenauer, Jon, et al., "A Non-Contact Imaging-Based Approach to Detecting Stage I Pressure Ulcers," Proceedings of the 28th IEEE EMBS Annual International Conference, New York City, Aug. 30-Sep. 3, 2006, pp. 6380-6383.
Sonenblum, Sharon Eve, et al., "Non-Invasive Erythema Detection Using Spectral Imaging," Proceeding of RESNA 2005 Annual Conference, Atlanta, Georgia, (2005), 8 pages.

\* cited by examiner

INTEGRATED PATIENT BED SYSTEM

CROSS-REFERENCE TO RELATED APPLICATIONS

This application claims priority to U.S. Provisional Application Ser. No. 61/049,243, filed Apr. 30, 2008, and U.S. Provisional Application Ser. No. 61/146,223, filed Jan. 21, 2009, the entire contents of which are incorporated herein by reference.

TECHNICAL FIELD OF THE INVENTION

The present invention relates in general to the field of patient diagnosis, monitoring and treatment, and more particularly, to an integrated patient system that interfaces with existing technology to improve patient care.

STATEMENT OF FEDERALLY FUNDED RESEARCH

None.

BACKGROUND OF THE INVENTION

Without limiting the scope of the invention, its background is described in connection with devices that aid in patient diagnosis, care and treatment.

Modern day decubitus ulcer prevention involves inexact nursing protocols and a variety of questionable products lacking clinically verifiable patient outcomes. This situation is today's reality despite the fact that several hundred thousand cases of decubitus ulcers are reported each year in the United States alone, comprising an estimated $13 billion dollars of associated healthcare costs. Currently, no standardized care protocol has been accepted for ulcer prevention, and nurses are largely left with the physical burden of moving the patient every two hours while visually observing the skin for signs of obvious breakdown.

Alternatively, specialized bed surfaces (i.e., mattresses) are often used that rest on a frame and provide direct patient support over relatively small ranges of motion. Their primary function is to alleviate the pressure commonly found in a patient's head, back, buttocks, and heel areas. To reduce ulcer risk, patient positioning may be performed via a set of hinges, slides, and motorized articulations; enabling poses such as flat, Trendelenburg (normal and reverse), vascular (raised legs), dining/sitting, and upright transitioning. Beyond the various positions defined, bed surfaces are commercially available in a wide range of cost and sophistication (major categories including passive foam/gel mattress; passive multi-chamber fluid/pneumatic systems; open-loop active pneumatics; and closed-loop active pneumatics) that may utilize pressure, displacement and strain sensing technologies to adjust individual chamber pressure. However, the problem with every existing approach lies in the reliance on the nurse to observe signs associated with dead tissue. By the time that the visual degeneration is noticed, substantial tissue death below the skin surface has already occurred. This delayed detection results in decubitus ulcers that, once treated, may take two years to return to original tissue health. As a high-cost and high-volume problem in hospitals today, care protocols must move away from efficient treatment towards automated and effective prevention of decubitus ulcers.

SUMMARY OF THE INVENTION

The present invention includes devices, systems and methods for improving patient monitoring and treatment. The present invention includes an Integrated Patient Bed System (IPBS). The IPBS is a fully automatic, fully instrumented, software supported, programmable unit that allows execution of treatment protocols with improved quality, safety, and efficiency with minimal human intervention. The IPBS is able to interact with existing patient care equipment and system and its architecture permits the system to communicate with devices to deliver specific patient treatments.

One embodiment of the present invention is a patient support system that includes a patient support, an electromagnetic detector positioned to detect one or more parameters of a patient's tissue health, wherein the detector measures or assesses tissue in contact with or adjacent to the patient support; a processor connected to the detector that stores one or more parameters of the tissue's condition that are indicative of tissue health, wherein an indication of tissue health is used to change conditions at or about the site of tissue contact. In one aspect, the processor is connected to one or more support repositioning devices that automatically move the patient if a change in tissue health is detected. In one aspect, portions of tissue that show a change in tissue health are marked with a fiducial for continued monitoring. The processor may be connected to one or more devices at the patient support that heat, cool, increase/decrease humidity, alter systemic pharmaceuticals, increase oxygen delivery, decrease pressure, or increase pressure of the tissue at or about a site in need of treatment. In one aspect, the patient support comprises a hospital bed. In one aspect, the electromagnetic detector includes a transceiver that emits waves and detects wave reflections from the patient's tissue, wherein the wave emissions and reflections are selected to traverse one or more substrates positioned between the array and the patient's tissue. The electromagnetic detector may detect electromagnetic waves that are visible, infrared, near infrared or hyperspectral. In one aspect, the electromagnetic detector detects signals that the processor converts into at least one measurement of change in tissue conditions, wherein the at least one measurement is selected from tissue blood flow, tissue oxygenation, tissue temperature, tissue humidity, tissue compression, tissue shear or combinations thereof.

In another aspect of the present embodiment, the processor further stores additional patient data selected from patient age, gender, weight, patient blood pressure, tissue oxygenation, body temperature, humidity or combinations thereof over time. This data compilation allows the creation of one or more images of locations for therapy prior to tissue degradation, during treatment of tissue degradation or following treatment for tissue degradation. In one aspect, the processor generates an image of the potential tissue degradation on the patient's body for use in treating the tissue prior to tissue deterioration. Examples of electromagnetic detectors include spectral imagers, digital sensors, analog sensors, charge coupled device sensors, charge injection sensors, linear scan sensors, surface acoustic wave sensors, quartz crystal resonators, metal oxide sensors, dye-coated fiber optic sensors, dye-impregnated bead arrays, micromachined cantilever arrays, chemically-sensitive resistor or capacitor films, metal-oxide-semiconductor field effect transistors, infrared sensors, ultraviolet sensors, and bulk organic conducting polymeric sensors. In another aspect, the patient support comprises an array of chambers, wherein a pressure within each chamber can be varied individually or in groups.

Another embodiment of the present invention is an integrated system for patient treatment, the system that includes a hospital bed, a plurality of patient diagnostic and treatment devices connected to a network, wherein each of the devices can communicate to a network and exchange information with the network about the care of a patient, and a processor accessible adjacent to the bed and connected to the network to integrate information obtained from the devices through the network with one or more additional sources of information databases, wherein the processor can communicate to one or more patient treatment devices either directly or via the network and the processor directs the one or more patient treatment devices to change the treatment of the patient. In one aspect, the one of the one or more patient treatment devices include at least one of a ventilator; a vacuum hose; an intravenous pump; a catheter; a dialysis machine; a blood occlusion regulator; an oxygen administration device; an infusion unit; and a nitrous oxide administration device; a chemotherapy device; a radiotherapy device; an enteral feeding device; or a defibrillator. In one aspect, the one of the one or more patient diagnostic devices is at least one of a hematology measuring device, a sphygmomanometer; a tonometer; an electroencephalograph; an impedance cardiography device; a carbon dioxide measuring device, a pulse oximeter; an electrocardiogram; a bispectral index; a scale; a pressure, flow and/or volume measurement device; a non-invasive blood pressure device; an invasive blood pressure device; a thermometer; a transcutaneous Doppler device; a transesophageal Doppler device; or a fluorescence activated cell sorter; a conductance meter or a hyperspectral imager. The system may also include a monitor in communication with the processor to display a patient's condition. In one aspect, the processor communicates with treatment devices that directly vary the rate of administering an intravenous fluid, a ventilator, a defibrillator, or a dialysis machine based on at least one of the following: the heart rate, the temperature of the patient, weight of the patient, electrical activity of the brain, the rate of the patient's breathing, the amount of collected urine, the analysis of the patient's blood, the dialysis treatment, blood pressure and the blood oxygen saturation. In one aspect, the processor directly provides heating or cooling to the patient based on the patient's body temperature needs, including environmental control immediately surrounding the patient or within the patient's room.

Another embodiment of the present invention is an integrated system for patient treatment that includes an electromagnetic detector positioned to detect one or more parameters of a patient's tissue health, wherein the detector measures tissue in contact with or adjacent to the patient support, a processor connected to the detector that stores one or more parameters of the tissue's condition that are indicative of tissue health, wherein an indication of tissue health is used to change conditions at or about the site of tissue contact; and a plurality of patient diagnostic and treatment devices connected to a network, wherein each of the devices can communicate to a network and exchange information with the network about the care of a patient; and a processor accessible adjacent to the bed and connected to the network to integrate information obtained from the devices through the network with one or more additional sources of information databases, wherein the processor can communicate to one or more patient treatment devices and the processor either directly or via the network directs the one or more patient treatment devices to change the treatment of the patient. In one aspect, the system may further include a storage media or display monitor in communication with the processor to store the patient's tissue health information. In one aspect, the processor is connected to one or more support repositioning devices that automatically move the patient if a change in tissue health is detected. In another aspect, the portions of tissue that show a change in tissue health are marked with a fiducial for continued monitoring. In another aspect, the processor is connected to one or more devices at the patient support that heat, cool, increase, decrease humidity, systemic pharmaceuticals, increased oxygen delivery, decrease pressure, increase pressure of the tissue at or about a site in need of treatment. In yet another aspect, the one of the one or more patient treatment devices comprise at least one of a ventilator; a vacuum hose; an intravenous pump; a catheter; a dialysis machine; a blood occlusion regulator; an oxygen administration device; an infusion unit; and a nitrous oxide administration device; a chemotherapy device; a radiotherapy device; an enteral feeding device; or a defibrillator. Examples of patient diagnostic devices include at least one of a hematology measuring device, a sphygmomanometer; a tonometer; an electroencephalograph; an impedance cardiography device; a carbon dioxide measuring device, a pulse oximeter; an electrocardiogram; a bispectral index; a scale; a pressure, flow and/or volume measurement device; a non-invasive blood pressure device; an invasive blood pressure device; a thermometer; a transcutaneous Doppler device; a transesophageal Doppler device; or a fluorescence activated cell sorter; a conductance meter or a hyperspectral imager. In another aspect, at least one of the plurality of devices is a monitor for displaying a patient's condition.

In one embodiment, the present invention includes a patient imaging system that includes one or more x-ray detector panels that are integral with a support, wherein the panels provide support for a patient, an x-ray source that emits x-rays towards at least a portion of the patient, and a processor in communication with the x-ray source and detector that allows a user to select which portion of portions of the x-ray detector are used for image capture. Thus, the present invention streamlines the physical involvement of x-ray procedures without exposing the patient to unnecessary radiation. In one aspect, a storage media or display monitor in communication with the processor stores the patient's imaging information. In another aspect, the support further comprises a scale connected to the processor and the processor uses the weight to predetermine the kVolts of x-rays delivered to the patient. The processor is connected to one or more devices connected to a patient including, but not limited to, a ventilator, an oxygen measurement device, a carbon dioxide measuring device, a pulse oximeter; an electrocardiogram; a bispectral index; a scale; pressure, flow and/or volume measurement device; NIBP value (blood pressure measured with a cuff); IBP (blood pressure measured with a cannula in a blood vessel); temperature measuring device; cardiac output device; blood occlusion regulator; oxygen administration; infusion units; and a nitrous oxide administration device.

In one aspect, the x-ray panel provides all of the support for the patient, wherein the entire body of the patient can be x-rayed without repositioning the patient. Alternatively, the x-ray image may be directed over adjacent panels or over a subset of a panel corresponding to a body portion of the patient. The system may further include at least one device that indicates where a specific portion of the body of the patient is positioned on the support. The system may also include location tags that are placed on the patient to indicate where different body parts of the patient are positioned on the support. In one aspect, the support is a hospital bed. The system may also include an integrated display that dynamically changes the x-ray image as it moves over the corresponding body part of the patient. In one aspect, the x-ray detector is a fluoroscope.

In yet another aspect, the x-ray detection panel is a full body, single-use, disposable x-ray film that is placed on a patient support and the user is able to twist, bend and shape the x-ray film around the patient such that specific locations of the patient (including if necessary the entire patient) such that an x-ray image is obtained. Within the carrier, multiple films, which may overlap, are positioned to provide complete patient coverage but that are the length and width that fit within common film developing equipment. Each film may include indicia that may be used to align the films back into the correct order. The carrier may be disposable or sterilized and reused. The present embodiment will be particularly useful in cases where trauma to multiple parts of the body are suspected (or in situations of patient unconsciousness), multiple wounds are suspected or additional information is required.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
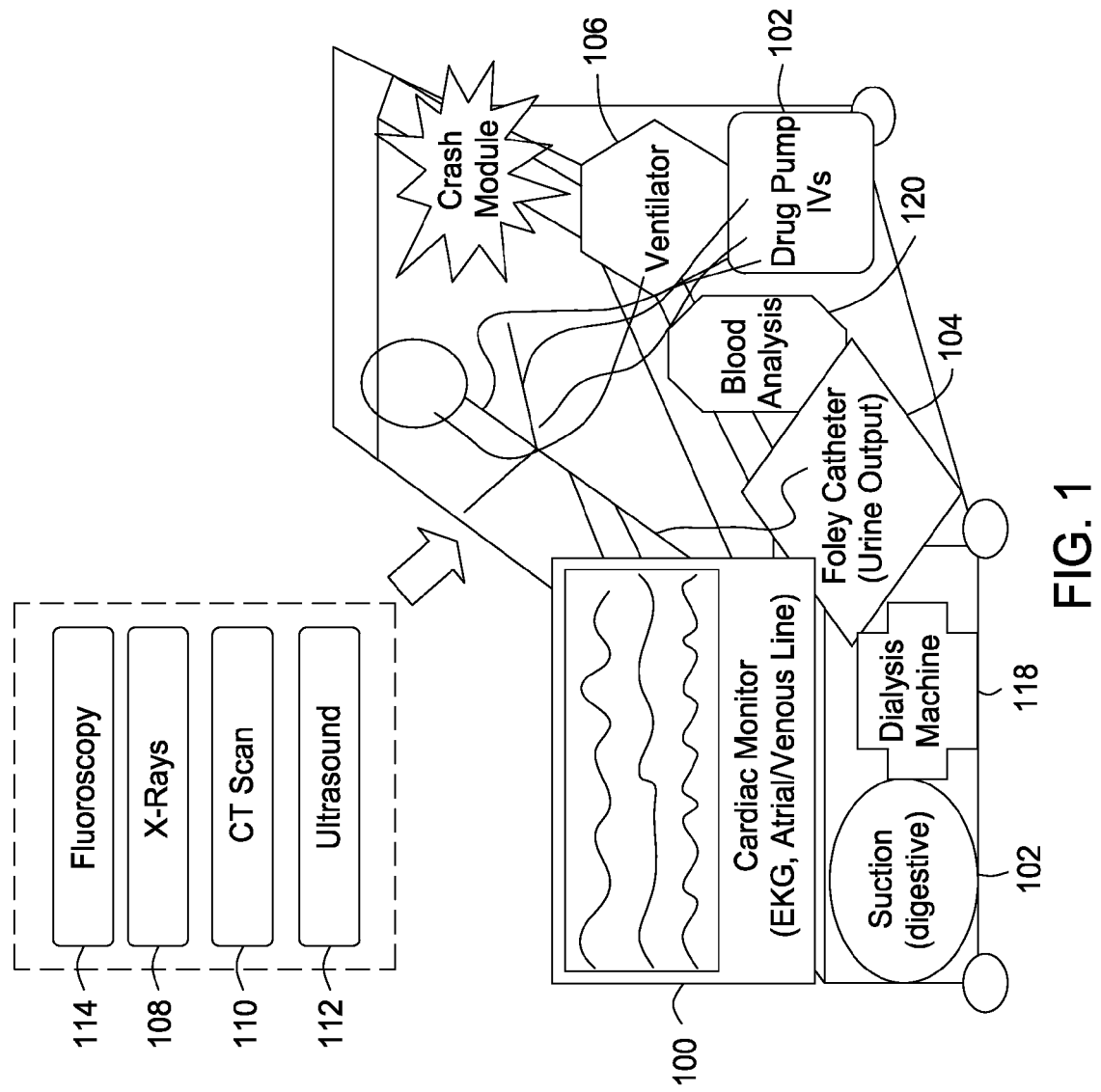
FIG. 1 illustrates a simplified diagram of a patient with the types of typical medical devices connected to the patient.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Current medical diagnostic and treatment devices needed to implement a given clinical treatment are based on proprietary systems and software that provide limited connectivity and communications. While, many medical devices now include external communications systems, these also tend to be proprietary. Furthermore, while industry efforts continue to develop standards for external communications, medical device manufacturers can be expected to resist widespread usage of standards-only solutions as such solutions can tend to commoditize the products of these manufacturers. It would be preferred to have fully-integrated, diagnostic and treatment systems, however, most care facilities already have capital investments in devices that are not integrated. Furthermore, physicians, nurses and medical care facilities often prefer to source medical devices from multiple vendors due to preferred features, pricing or familiarity with certain systems.

Acute care is a growing part of the current healthcare industry. As insufficient insurance coverage abounds, more people rely on acute care facilities for their medical needs. With the rise in demand and the lack of sufficient care resources, the need for efficiency and streamlined solutions is imminent and necessary. IPBS answers this impending problem by providing an efficient and customizable solution to serve the varying demands of critically ill patients.

Acute care refers to the treatment of a disease for a short period of time in which a patient is treated for brief (yet severe) episodes of illness. Critical care involves a variety of key players, including (but not limited to), doctors, nurses, respiratory therapists, nutritionists, radiologists, and above all—the patient. The flow of care typical of an ICU is cyclical in nature with a dynamic treatment plan determined by the physician.

The present inventors recognized that a fully integrated medical device system or suite is unlikely due to the need to source medical devices from multiple vendors. As such, the present inventors have developed a system and methods to access existing devices that are capable of exchanging information between any network elements and can be used to provide integrated patient care assistance. The present invention allows existing healthcare devices to be used as part of the solution and allows manufacturers to maintain differentiated and proprietary communications functionality within their products. The present invention provides for event driven configurability including for effective disaster response.

Current technology requires significant human intervention for almost all the monitoring and care protocols the IPBS addresses. With use of the IPBS, the number of systems requiring frequent monitoring and manual recording of data are significantly reduced by automatically collecting the routine information, displaying it at the bedside while also communicating it to a central work station (and possibly other work stations, central storage and/or personal digital assistants). The IPBS is also able to interact with local and remote databases to gather, process and display patient information regarding medical events or conditions in the patient's past that are available to the medical professional. The IPBS allows patient care to be significantly improved by linking, controlling and monitoring patient diagnostic and treatment systems that are monitored automatically to not only current medical conditions but future expected patient outcomes. The IPBS also provides savings in human labor and an increase in patient safety and quality of care that is significant.

In addition, the IPBS also allows all of the medical devices/machines incorporated within or connected to the IPBS to transmit information in nearly real time to a centralized electronic health record (EHR) storage system. The locally based comprehensive monitor and semi-automated, and/or automated, clinical protocols of the IPBS are enabled at the bedside, by accessing both local equipment (when installed) and data from local equipment via remote EHR server(s). Since all of the equipment is made by different manufacturers and is compatible, all equipment contributes to the patient's EHR. Hence, the IPBS efficiently utilizes information from existing equipment/devices from a wide variety of manufacturers even if local connections to the equipment are not available, or if they use proprietary methods local to their devices.

Moreover, current care in the ICU is labor intensive, inefficient, and subject to human error. Simply moving the patient to get X-rays or CT Scans requires involvement of several members of the ICU team with great risk of an important connection being displaced or injury to the patient. In contrast, the IPBS allows the diagnostic tools to be accessed with improved safety while increasing the efficiency of personnel assigned to the ICU.

The IPBS also includes the ability to program a very large majority of the routine monitoring and diagnostic measurements to occur automatically, thus freeing up critical personnel for tasks that cannot be effectively automated (e.g. talking to patient's family). The IPBS also allows the physician to construct a protocol and a program unique to the needs of the physician and/or patient and be confident the program will be executed. Moreover, information is immediately available at the bedside and at the same time is archived in a central and/or remote location.

An x-ray generator for use with the present invention may include an automatic exposure control device in which a maximum exposure time and an exposure kV start voltage for the x-ray tube are preset. Once the x-ray exposure has been commenced, the exposure can be automatically controlled by measuring the x-ray absorption, for example, based on strikes at the x-ray detector. If the x-ray absorption is greater than a predetermined threshold, the exposure kV start voltage is adjusted. If the x-ray absorption is less than the predetermined threshold, the exposure time is adjusted while maintaining a constant exposure kV start voltage. A variation on this x-ray generator system adjusts the preset tube voltage within a certain window in which the operator selects a type of target or examination and directs the underlying tube voltage and current for the generator. When the exposure is initiated, by an operator or automatically by the IPBS system, the preset tube voltage and current settings are used unless the feedback system at the x-ray detector reaches its threshold. The feedback system is able to measures the dose rate and estimate the expected length of exposure. In some x-ray systems, tube voltage is preset via a user interface based on a large number of present combinations. The x-ray generator-detector pair of the present invention can be used to automatically adjusts the tube voltage during exposure, however, safety constraints can be added to kept exposure within certain preset minimum and maximum values.

X-ray detection for use with the present invention includes both film and electronic detectors, such as microchannel plate amplifiers, scintillators, phosphor plates, semiconductor detectors, proportional counters, single photon calorimeters and negative electron affinity detectors, to name a few. The integrated x-ray detector support of the present invention will find particular usefulness in situations where the user or IPBS system determines to take x-ray of a patient that is unable to move or be moved and/or in which multiple x-ray targets are found. Generally, the support and the x-ray detectors will be in the form of one or more panels, which may include some overlap between detectors so as to eliminate gaps.

X-ray proportional counters generally include a windowed gas cell, subdivided into a number of low- and high-electric field regions by use of electrodes. The signals triggered at the electrodes by the motions of electrons and ions in the counting gas mixture provide information about the energies, arrival times, and interaction positions of the photons transmitted by the window. Microchannel plates (MCPs) are compact electron multipliers of high gain. A typical MCP has about 10,000,000 closely packed channels with a common diameter that are formed by drawing, etching, or firing in hydrogen, a lead glass matrix. Semiconductor ionization detectors are primarily used as non-dispersive spectrometers of high energy resolution. Semiconductor ionization detectors use an array of detector types based on electron-hole pair creation in cooled silicon or germanium, or in a number of room temperature materials such as mercuric iodide. Scintillators and phosphors work by converting x-ray energy into visible light. Negative electron affinity detectors (NEAD) provide high spatial resolution, high quantum efficiency, and moderate energy resolution. NEADs use semiconducting compounds from the 3rd and 5th columns of the periodic table (e.g., GaAs) to activate a state of negative electron affinity after treating a surface with cesium and oxygen. Single photon calorimeters work by the low-noise conversion of absorbed energy to heat and include an x-ray absorber, a thermistor and a low-noise amplifier. X-ray causes a temperature rise that produces a voltage pulse at the thermistor and the change in temperature is measured.

The present invention also uses a variety of sensors for detecting changes in the health of tissue. For example, the sensors may be electromagnetic detectors such as spectral imagers, digital sensors, analog sensors, charge coupled device sensors, photomultiplier tubes, bolometers or microbolometers, charge injection sensors, linear scan sensors, surface acoustic wave sensors, quartz crystal resonators, metal oxide sensors, dye-coated fiber optic sensors, dye-impregnated bead arrays, micromachined cantilever arrays, chemically-sensitive resistor or capacitor films, metal-oxide-semiconductor field effect transistors, infrared sensors, ultraviolet sensors, and bulk organic conducting polymeric sensors.

The present invention also uses and communicates with one or more devices connected to a patient including a ventilator, an oxygen measurement device, a carbon dioxide measuring device, a pulse oximeter; an electrocardiogram; a bispectral index; a scale, pressure, flow and/or volume measurement device, NIBP value (blood pressure measured with a cuff), IBP (blood pressure measured with a cannula in a blood vessel); temperature measuring device; cardiac output device; blood occlusion regulator; oxygen administration; infusion units; and a nitrous oxide administration device.

The present invention also uses and communicates with one or more patient treatment devices including at least one of a ventilator; a vacuum hose; an intravenous pump; a catheter; a dialysis machine; a blood occlusion regulator; an oxygen administration device; an infusion unit; and a nitrous oxide administration device; a chemotherapy device; a radiotherapy device; an enteral feeding device; or a defibrillator.

The present invention also uses and communicates with one or more patient diagnostic devices including at least one of a hematology measuring device, a sphygmomanometer; a tonometer; an electroencephalograph; an impedance cardiography device; a carbon dioxide measuring device, a pulse oximeter; an electrocardiogram; a bispectral index; a scale; a pressure, flow and/or volume measurement device; a non-invasive blood pressure device; an invasive blood pressure device; a thermometer; a transcutaneous Doppler device; a transesophageal Doppler device; or a fluorescence activated cell sorter; a conductance meter or a hyperspectral imager.

The medical devices and the network and processor of the present invention are able to communicate with the various devices, environmental controls and provide information to medical personnel in the form of data, images, alarms and the like via wired or wireless connections. For example, the present invention is able to communicate with devices that operate using older implantable medical devices frequencies ranging from, e.g., 32 KHz to 175 KHz. The present invention is also able to communicate based on recently allocated frequency bands for use with wireless medical device communication, commonly referred to as the Wireless Medical Telemetry System (WMTS). The present invention can operated at the WMTS frequency bands, which include 608-614 MHz, 1395-1400 MHz, and 1427-1432 MHz. It is contemplated that additional bands may be provided for use by implanted medical devices commonly referred to as Medical Implant Communication Service (MICS) frequencies. MICS includes the 402-405 MHz frequency band. The present invention can communicate with medical devices using any of these frequency bands as well as using any of the wireless protocols that might be broadcast by the devices. Wireless communications include any electromagnetic wave, including light (e.g., infrared) and radio frequencies.

FIG. 1 shows a simplified diagram of an intensive care hospital bed, patient and a variety of medical devices. For example, four types of scanning devices are shown. In this embodiment, a fluoroscope 114, an X-ray machine 108, a Computed Topography (CT) Scan machine 110 and an ultrasound machine 112 are shown. In addition, a suction device 102, a ventilator 106, a catheter 104 and a few intravenous (IV) devices 102 are shown. Also shown are numerous vital sign sensors 100 that can include a transducer hub and cardiac monitor. Furthermore, other machines, such as a resuscitation cart, a blood analysis machine and a dialysis machine may be added to provide patient diagnostics and treatment (e.g., dialysis or intravenous administration of drugs). The skilled artisan will appreciate that FIG. 1 is a simplified diagram with certain medical devices; however, the present invention is able to communicate with any device having communications capability that may be brought into the patient treatment area that communicates with a network. Depending on the condition of the patient and the devices needed for the expected treatment, devices may be incorporated to the patient treatment area and allowed to communicate with the network.

Figure 2:
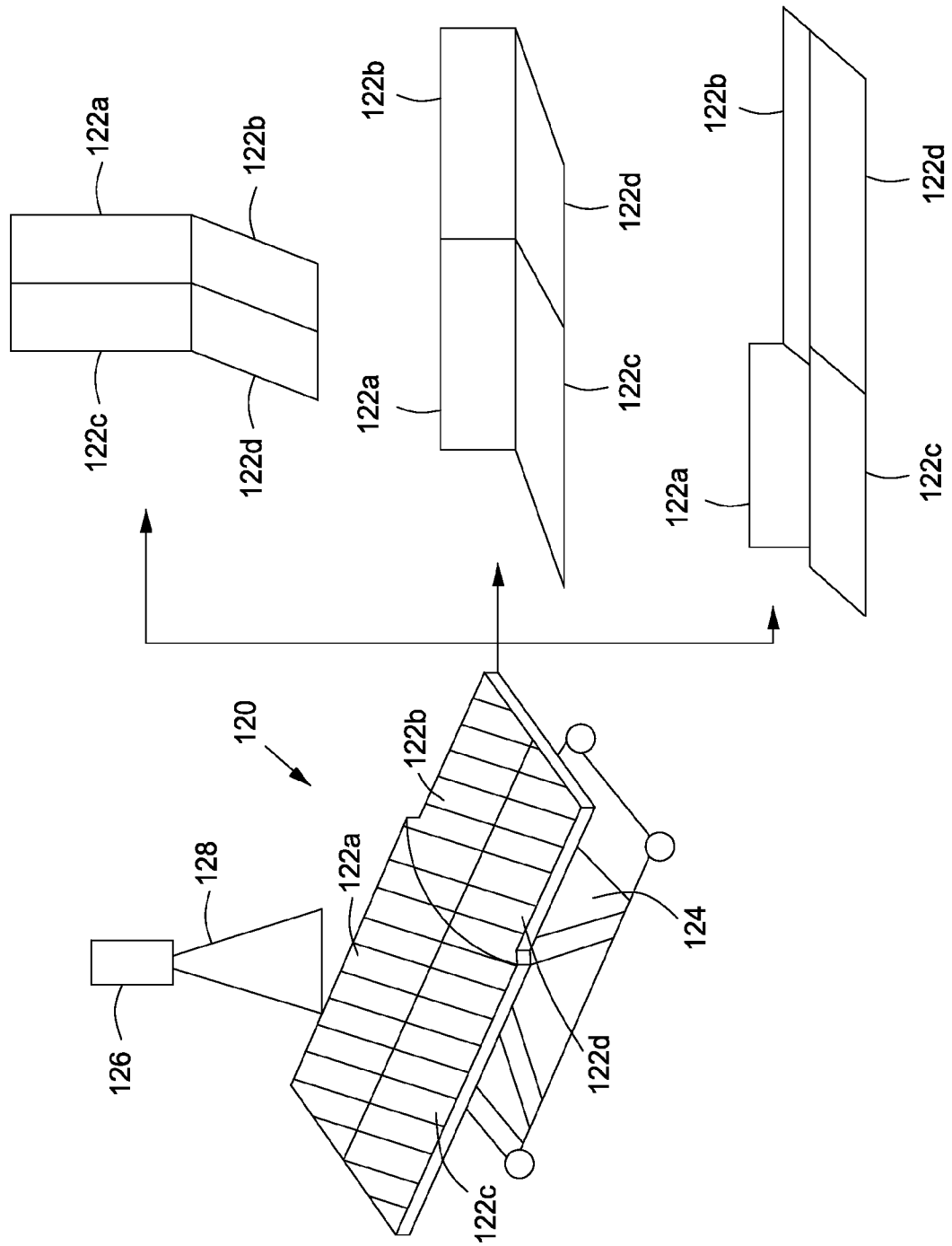
FIG. 2 shows the integrated patient x-ray system of the present invention.

FIG. 2 shows one embodiment of the patient imaging system 120 that include one or more x-ray detector panels 122*a-d* that are integral with a support, wherein the panels 122*a-d* also provide complete mechanical support for a patient. Also shown is a frame 124 on which the x-ray detectors are placed and may be placed on the frame 124 to form an integral part of the bed 124. An x-ray source 126 that emits x-rays 128 towards at least a portion of a patient (not depicted) is shown. A processor (not depicted) is in communication with the x-ray detector panels 122*a-d* that allows a user or system to select which portion or portions of the x-ray detector 122*a-d* will be used for image capturing. In one embodiment of the present invention, the panels 122*a-d* are depicted in various configurations that permit the user or system to either position the patient or allow the patient to remain in a fixed position while the x-ray source 126 is pointed at the location in need of treatment. The present invention provides a customizable configuration of the x-ray plate embedded within a support surface.

Figure 3:
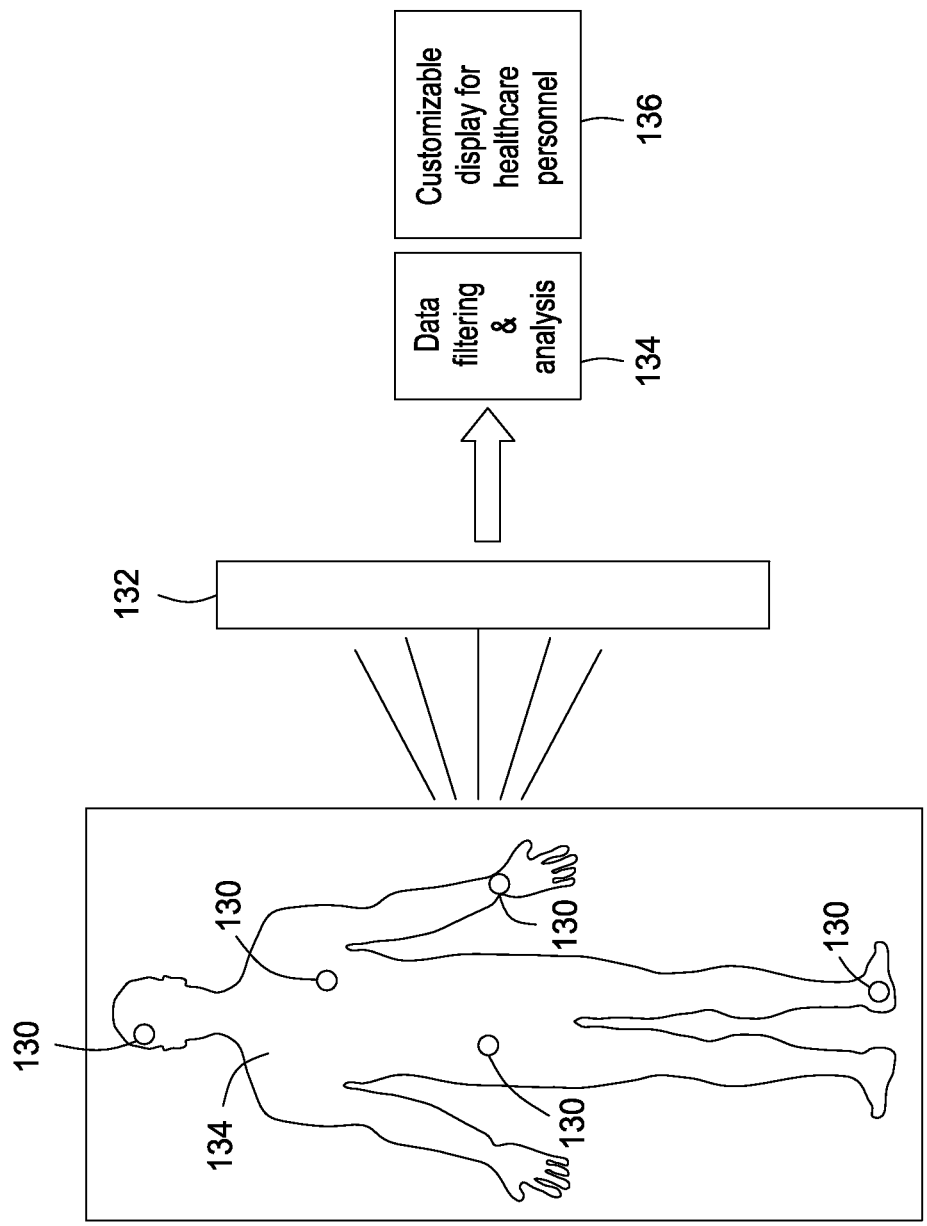
FIG. 3 shows one embodiment of the remote electromagnetic wave sensor embodiments of the present invention.

FIG. 3 shows a system for detecting and displaying tissue health. Examples of tissue health include degradation, deterioration, improvement or baseline conditions. In this example, the sensors 130 are not positioned on the patient 134, but are positioned on bed sheets or the mattress and communicate to a wireless receiver 132 and produces a graph 1904 for the care giver to examine in the form of a display 136.

Figure 4:
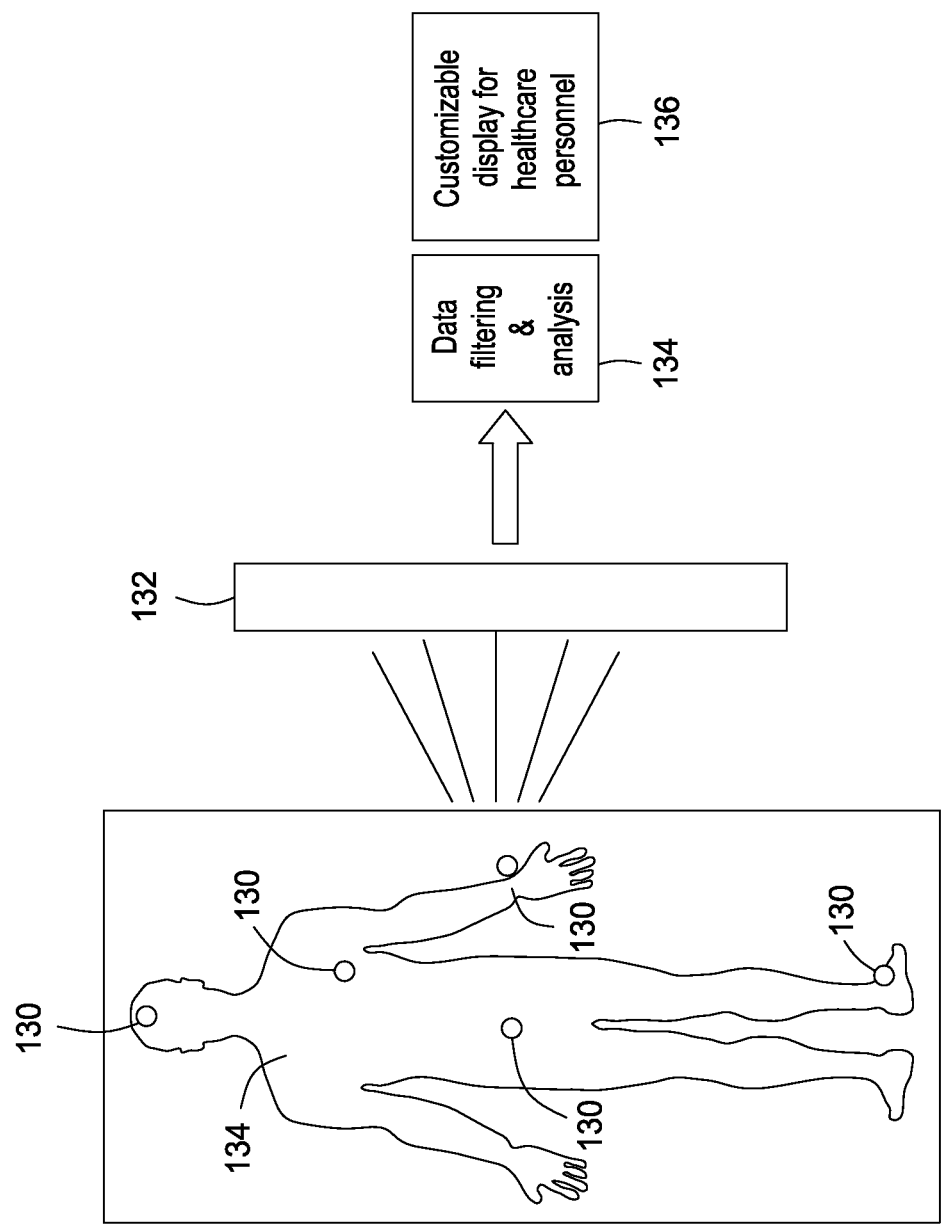
FIG. 4 shows another embodiment of the electromagnetic wave sensor embodiments of the invention in which sensors are placed on the patient.

FIG. 4 illustrates another example of detecting and displaying tissue health. In this example, the sensors 130 are positioned directly on the patient 134. However, similar to FIG. 3, the sensors 130 communicate to a wireless receiver 132 that is used to filter, analyze (box 134) and display 136 which can display a graph 134 for the care giver to examine.

Figure 5:
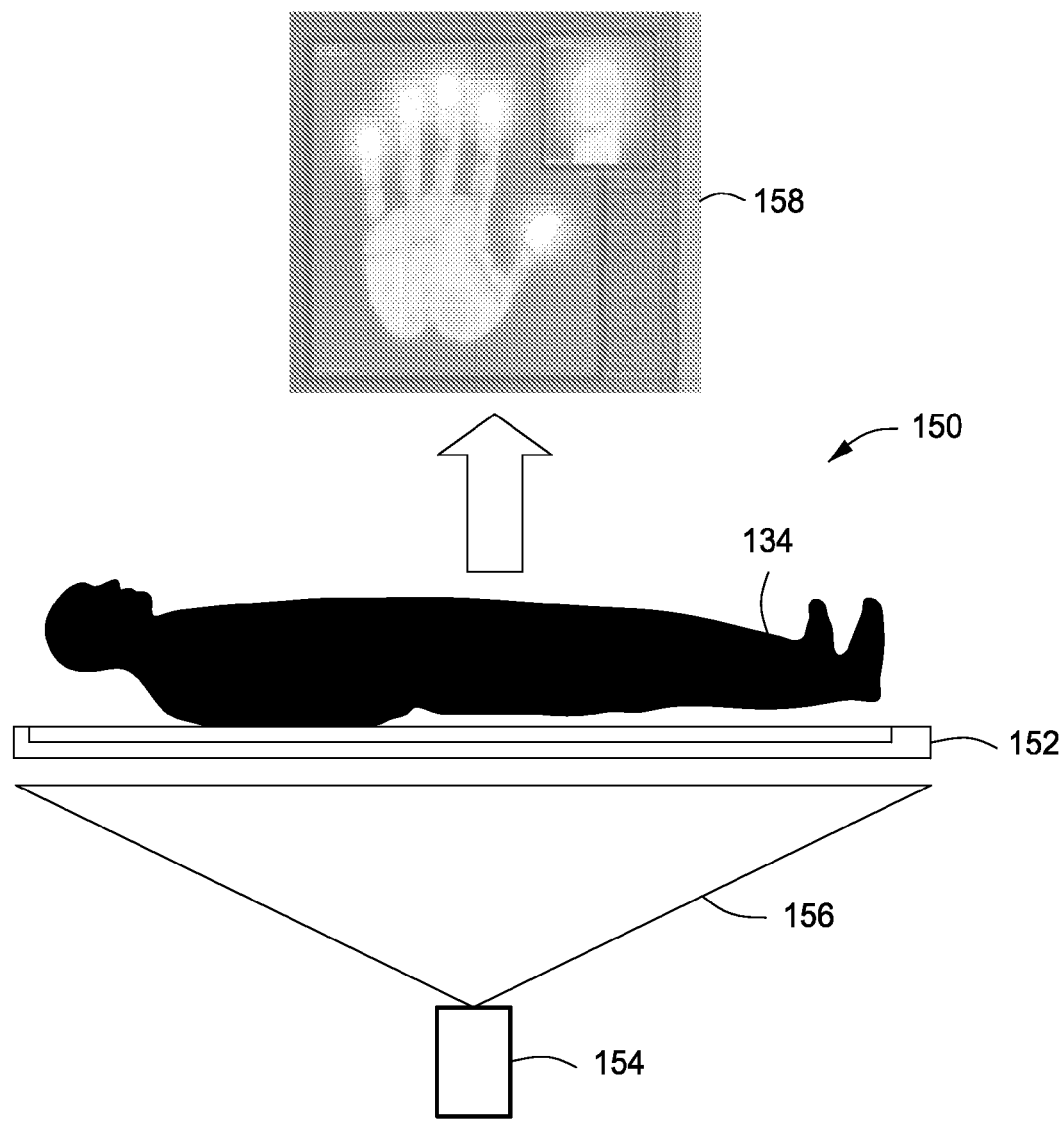
FIG. 5 shows a hyperspectral imaging embodiment of the present invention.

FIG. 5 shows an imaging system 150 in which the patient 134 is positioned on a support 152. An electromagnetic detector 154 is positioned to emit and/or detect one or more parameters of a patient's tissue health, wherein the detector measures tissue in contact with or adjacent to the patient support 152.

The electromagnetic detector 154 emits or receives electromagnetic waves 156 from any part of the electromagnetic spectrum, e.g., visible, infrared, near infrared, ultraviolet, hyperspectral, microwave or ultrasound, that will be selected on the parameters of tissue health that are to be measured to determine and track tissue health. Generally, wavelengths will be selected that permit the waves to traverse support structures and/or support covers (e.g., pads, linens, plastic) and in which the detection is sufficient to determine tissue health. Tissue health as used herein includes the various layers of the integumentary system (epidermis and dermis, such as stratum corneum, stratum granulosum, stratum basale, basement membrane), muscle and even bone. Generally, a processor connected to the detector 154 that stores one or more parameters of the tissue's condition that are indicative of tissue health, wherein an indication of tissue health is used to change conditions at or about the site of tissue contact. The processor is also able to display 158 the image of the target, in this case, patient 134.

The medical information for the patient is directed to the processor in which, medical device transceiver(s), data relay transceiver(s), and a memory are coupled to the processor for storing instructions. The medical data transceiver is configured to receive data wirelessly from one or more medical devices. The processor executes the instructions in the memory to receive data from one or more medical devices using the plurality of medical device transceivers (which gathers data concerning the patient's condition from the devices as well as any information available from the patient obtained from local and remote servers), and transmits the data to an intermediary device using the data relay transceiver. The processor is also able to encrypt the data. The data can be encrypted using a combination of public and private keys to allow sensitive patient medical data to be transmitted securely to medical service providers.

The Integrated Patient Bed System (IPBS) offers an innovative, systems-based solution to many important clinical and operational problems present within the current healthcare system. By leveraging novel technologies and advanced semiconductor solutions in the context of a systemic architecture, IPBS provides a scalable, functional, and practical answer to a complex problem.

Limited availability of interconnected and intelligent electronic systems in the acute care environment leads to operational issues such as overworked nurses, preventable medical errors, and operative incompatibilities. Changes in recent insurance policies denying reimbursements of preventable medical errors have heightened the interest and investment in this area. In 2006, according to the Center for Medicare Services, $15.6 billion in hospital costs were incurred nationwide due to preventable medical errors that IPBS can directly reduce. Such errors include pressure ulcer formation, ventilator associated pneumonia, and falls and traumas. These preventable errors can be linked to problems within the critical care environment including facilitating patient movement, limited patient monitoring, efficient and timely administration of treatment, and delayed or inaccurate communication between various healthcare personnel. Rather than address each issue individually, IPBS understands critical care as a system and creates a solution that vertically and horizontally integrates the care process to address these specific needs.

IPBS improves operational workflows, enhances patient outcomes, and reduces operational costs by creating solutions in the following areas: seamless integration of diagnostic capabilities; clinically intelligent patient positioning; wireless interconnected patient monitoring and treatment solutions; and clinical informatics and automation of clinical protocols.

The seamless integration of diagnostic capabilities imbeds X-ray, ultrasound, and spectral imaging technology within the patient bed. Moving away from the bed as a physical entity surrounded by technology, IPBS works to utilize the bed as a useful technological component of the patient care system incorporating key sensor, data conversion, image and signal processing, power management, storage, display, and wireless communication devices. The integration of X-ray technology within the bed provides convenience for nurses, radiologists, and physicians when conducting examinations by targeting specific areas of the body without having to move the patient and providing timely data at the patient's bedside.

In addition to improvements upon existing technologies, IPBS incorporates traditionally non-medical technology (i.e., spectral imaging) to the critical care setting. As a novel method to assess various metabolic and tissue-level parameters, spectral imaging has potential to serve as a powerful diagnostic tool for physicians. IPBS provides for the first time real-time assessment of tissue health and degeneration and provides systems and methods for automatically and intelligently managing patients in real-time for skin ulcer prevention and wound care treatment.

The application of spectral imaging links directly to efforts to automate the intelligent positioning of patients within the bed. As wound care management and pressure ulcer prevention are large and expensive concerns in acute care settings, the importance of clinically driven protocols is paramount. By automating and intelligently assisting the nurse in patient movement, the physical burden on the critical care nurse is greatly reduced and patient care is vastly improved through optimized prevention methods.

The wireless implementation of patient monitoring improves the ergonomics of the patient care room, facilitate patient movement, and most importantly improve the methods of communication while reducing errors that typically occur during miscommunication of physician orders. While multiple wireless solutions currently exist, IPBS uniquely works to create a network-based interoperability solution enabling use of existing medical devices and information systems. By working within the current equipment framework, IPBS conforms to existing infrastructures rather than requiring total replacement of existing capital investments.

IPBS creates a feasible and affordable solution that can be implemented within the current healthcare system, leveraging innovations in physiologically based patient re-positioning, integrated diagnostics and decision assistance through network interoperability, to overcome limitations of the present healthcare process, thus avoiding unnecessary costs to hospitals, while enabling better, safer patient care.

The automation of intelligent patient positioning, while answering the specific problem associated with pressure ulcers, falls under a larger scope of the IPBS in automating clinical protocols and physician directives. To automate clinical protocols via medical equipment, systems interoperability must be readily achieved. By creating a quasi-open array of medical equipment, a wireless standard can be implemented to streamline data acquisition between different wards and healthcare providers. In creating a wireless protocol, both physical and informational access to the patient is vastly improved for more streamlined patient care.

The IPBS also serves to create an interoperable infrastructure within the acute care patient room that provides intelligent feedback for the prevention of medical errors. By creating communicative pathways between equipment such as ventilators, EKG machines, and drug pumps—certain clinical protocols originally administered by the critical are nurse can be shifted to an automated system to increase the amount of time nurses have for direct patient care.

In operation, once the intensive care protocol is triggered, an attending physician conducts a thorough physical examination to assess the critical condition of the patient and determine an appropriate treatment. Physician directives include prescribing medications, ordering diagnostics such as labs and imaging, and implementing treatment such as feeding tubes and ventilator support. This protocol is then executed and/or monitored by a group of healthcare professionals that remain in communication with each other. As critical care nurses continuously monitor patients, they provide the most up-to-date patient information and execute the majority of clinical protocols. Due to the complexity of ICU patient care today, Registered Nurses (RNs) are typically assigned to two patients (and sometimes one for severely ill patients or early post-operative patients) during a given shift. While a 2:1 ratio is sufficient for patient monitoring, other seemingly simple tasks such as moving the patient within the bed or throughout a hospital involve multiple hospital personnel depending on the severity of the illness and patient's body weight. As treatment is administered, attending physicians and residents monitor the progress of each patient several times throughout the day. Physician directives change according to a patient's response, and the efficacy and accuracy at which these reassessments are completed plays a large role in patient improvement. Once the patient is deemed stable, the attending physician orders a transfer to the telemetry ward for less rigorous monitoring until the patient can be discharged.

While advancements in underlying semiconductor and component technologies have enabled corresponding enhancements and acceptance of electronic medical devices and information technology networks within healthcare facilities, the lack of a comprehensive systems approach to the problem limits the ultimate effectiveness of present day hardware and software products in practice. As such, the full benefits of improvements in monitoring, diagnostic, therapeutic and mechanical medical devices have not been realized. Current technologies still require significant human intervention for many common monitoring and care protocols, and lack of interoperability between therapeutic and diagnostic equipment adds significantly to care inefficiencies as well as opportunities for mistakes that impact patient safety.

The IPBS solution provides this systems-based approach necessary for the efficient delivery of healthcare and maintenance of patient records. Harnessing available technology components, IPBS serves to simplify the complexity of the healthcare system that leads to operational issues such as overworked nurses, preventable medical errors, and operative incompatibilities. To best understand the critical care needs, the following section details the issues that arise within each category of patient care: (1) patient movement/transport, (2) monitoring, (3) diagnosis, (4) treatment & resuscitation, and (5) administrative/communicative protocols.

Patient Movement/Transport. Patient mobility may be impaired directly by therapy (i.e. surgical anesthesia or use of paralytic drugs for ventilator-assisted patients) or as a consequence of the patient's health problem (traumatic injury, coma, acutely debilitating disease). These patients are typically confined to bed and are thus at greater risk for pressure ulcers. Pressure ulcers form from the lack of blood flow near bony prominences that bear the most weight of the bedridden patient. The immobility combined with the patient's debilitated state significantly increases the risk for pressure ulcers. In response to such risks, nurses are given the responsibility of moving the patient every two hours to prevent such problems. The physical burden placed on the nurse is quite exhausting, particularly for bariatric patients in which multiple nurses are involved in adjusting patient positions. Beyond the difficulty of moving the patient, no current system exists to determine what patient movement best prevents ulcers. Physical therapists are not available for all patients, and nurses move patients based on their own experience and judgment.

Transport during a patient's length of stay is typically required for either obtaining diagnostic exams (X-Ray, CT, ultrasound scans) or transferring patients to different wards as health status improves. This process can take from 30 minutes beyond, involving a team of professionals including the respiratory therapist, nurse, transport technicians, and any additional nurses/residents for severely ill or overweight patients. The patient must be disconnected from the permanent room equipment to portable devices, transported onto a stretcher or gantry, transported to a different ward, and then reconnected. The critical care nurse is left with the responsibility of disinfecting wires and re-adjusting the patient to the new environment.

The IPBS resolves these issues by providing transportable and seamless interfaces that do not interfere with existing clinical protocols. To reduce the physical involvement of the nurse, a system must be created that collects both intrinsic and extrinsic environmental factors with respect to the patient's condition and connect to an automated control system to enact the patient movement required for pressure ulcer prevention and wound care management.

Monitoring. Acute care requires 24-hour surveillance of the patient's physical condition that is collected via an array of monitoring equipment. The lack of wireless integration of various sensors (blood pressure, ECG, $O_2$, $CO_2$) immobilizes the patient due to the extent of connections required. Additionally, these monitors do not incorporate existing clinical protocols to create an intelligent feedback system. Any abnormal fluctuations in metabolic levels or pressures are not logged unless caught by the critical care nurse on the hourly rounds or with trigger alarms at the central nursing station. In addition to the system flaws within patient monitoring, correlations between therapeutic equipment (i.e. ventilators and medications) and parameters such as blood pressures, $SpO_2$, and $SpCO_2$ are not typically made.

To appropriately support the medical care provided, an interface must be created to intelligently discern between abnormal physiological fluctuations and external artifacts (i.e. accidental pressure placed on tube or intentional disconnection of wires). Once accomplished, this intelligent monitoring system would then present the physician with relevant patient information that would have otherwise gone unnoticed.

Diagnostics. Beyond the physical exam conducted by the physician, supporting exams (i.e. X-ray, fluoroscopy, ultrasound, CT) ensure accurate diagnosis and subsequently accurate treatment of severe diseases. The main issue involved with diagnostic equipment is the necessity to transport the patient to clinics specific to imaging techniques. As mentioned previously patient movement and transport is a long, involved, and dangerous process that would ideally be avoided or minimized.

The present invention integrates diagnostic mechanisms such as x-ray imaging, certain transportation orders can be avoided completely. The results of diagnostic exams must prove equivalent to current standards in both accuracy and precision. Ideally, 95% of diagnostic images taken via the integrated imaging technique would prove comparable to images acquired at clinics dedicated to medical imaging.

Treatment, e.g, resuscitation. The improvement of a patient's condition relies upon the efficient administration of treatments ordered by the attending physician. For example, a defective treatment implementation may go undetected because the therapeutic device cannot communicate to existing monitoring equipment. More specifically, if a nurse does not realize that a patient has awoken, respirator settings may continue at incorrect levels that were set when the patient was at rest, despite available monitoring information that could enable a more timely automated or semi-automated adjustment for the patient, if its feedback to the respirator were readily available. In providing a streamlined, feedback-enabled work environment, treatment protocols can be adhered to more strictly and unnecessary treatments can be avoided via the more accurate monitoring of treatment results.

Due to the uncertainty of patient outcomes in an acute care setting, all emergency and intensive care units are supplied with a crash cart that includes a defibrillator to shock the heart and medications available in emergency-level doses. Despite the immediacy required in emergency response situations, these crash carts are bulky and must be transported to the patient's room before being utilized. A simple integration of emergency care protocols within the Integrated Patient Bed System is readily achievable and necessary.

Administration and Communication. Multiple professionals are involved in the care of one patient, therefore, the communication between each caregiver must remain both constant and accurate. Currently, patient notes are typically compiled within a patient binder available by the patient's bedside. While online patient databases are available, professionals rely on paper records for the most up-to-date patient information. This limitation becomes apparent when looked upon within the context of a clinically driven patient care protocol. An attending physician will typically write a set of care instructions for the ICU RN to follow. These directives often require the RN to manually manipulate distinct equipment, acquire and affix pharmaceuticals, note possible drug interactions, all the while taking care to document information for the benefit of the attending physician, next shift nurse, and hospital administration. Given the stresses present in ICU environments and the number of distractions typical thereof, it is not surprising to discover that mistakes are common. Issues arise when misplaced decimal points on written documentation can result in a dramatically different conclusion on the well being of the patient. If left undiscovered, such errors may result in unneeded or incorrect patient treatments.

The present invention enabled intelligent communication between monitoring/diagnostic and therapeutic equipment, the need for manually changing equipment settings could be eliminated. The automation of certain clinical care protocols could prevent errors such as misplaced decimal points and reduce lag-time characteristic of orders administered by the attending physician. In providing a wireless solution, IPBS would be capable of providing a secure channel for more rapid, efficient transmission of information to physicians to monitor, respond to perturbations, and accordingly adjust orders.

Seamless Integration of Diagnosis. Accurate diagnosis is an integral part in providing quality healthcare to the patient. Without the appropriate tools to assess the health status of the patient, the appropriate prognosis or treatment will be missed. While the diagnosis of a patient is heavily reliant on the acuity of the doctor, the supporting medical exams are utilized to corroborate and more accurately define the doctor's diagnosis.

Current methods involve shifting the patient to a diagnostic room rather than designing diagnostic equipment to conform to the patient. Existing ultrasound technology does provide portable tissue and organ imaging systems; thus allowing the integration of existing ultrasound techniques within the IPBS. While ultrasound techniques have partially answered the need for seamless diagnostic mechanisms within a patient room, existing x-ray imaging do not fit over existing intensive care bed systems. Even where x-ray systems are somewhat portable, as in the case of C-Arm systems, it is required to bring a bulky piece of expensive stand-alone equipment to the patient's area, and re-position the patient for the imaging. In addition to harnessing current medical technology, the use of spectral imaging in a medical setting is an upcoming technology to be explored that would provide alternative methods to detect various chemical compositions within the body including blood perfusion, saturation levels, various chemical toxicities, and distinguish internal organ structures.

The present invention integrates various diagnostic modalities within the intensive care system to provide in situ imaging integrated into the clinical informatics and decision assistance capabilities of the IPBS.

The IPBS includes an x-ray detection array panel that would be dynamically refreshable, long lasting, and rugged, extending beneath the entire patient support surface, with readout of the image directly to the IPBS console. This integration within the IPBS involves an extensive systems-level design with specification of physical characteristics, interfaces, power requirements, x-ray flux requirements, resolution options, and other performance parameters.

The present invention also allows for the integration of spectral imaging. While the basic concept remains the same, the potential for clinical applications for the analysis of tissue health, care and treatment before decubitis lesions form has never been achieved. Hyperspectral data works via the absorption of many bands of light intensity within each pixel, thus creating a specific signature to each chemical component. As spectral data is used to determine what materials are present in a scene, similarly, the medical application would determine what chemicals are present within the patient's body.

For example, an integrated spectral image is used to determine tissue health. The image data can be used to establish a treatment regimen in a critical care environment based on the health care professional's selection of medical devices within the patient environment. For example, the distance from the patient and lens orientation can change the spatial resolution and sampling area obtained. In addition, software adjustments such as sampling rates and image filtering would be designed towards providing the physician with an overview of the patient's progress and status. In addition to the reduction in patient transportation, the present invention allows the user to integrate various diagnostics into one display to the physician should improve diagnostic information to better empower the care provider in creating a plan of care.

Systems interoperability and clinical informatics. Current acute care patient rooms are not feedback-enabled to provide intelligent assistance to healthcare providers. Accumulation and processing of monitoring and treatment data is solely dependent on the critical care nurse. This data collection is crucial to the attending physician and residents in providing the appropriate alterations to treatment protocols and assessment of patient progress. By providing a system that reduces this administrative task, nurses can have greater time to provide direct patient care.

In the current healthcare model, the only form of integration of patient information occurs within the ICU ward at the Central Nursing Station where patient's vital statistics are constantly displayed on an array of monitors. If any of the patients within the ward exhibit dangerous fluctuations in cardiac parameters (i.e. systolic/diastolic blood pressure and heart rate), an alarm sounds for the nurses to check on the patient. While relatively primitive in nature, the basic idea remains the same—to provide technology to assist healthcare personnel in providing quality healthcare. Rather than making perfect decisions, the utilization of centralized patient information to automate clinical protocols will assist in creating better decisions, improve operational workflow, and ultimately enhance patient outcomes.

The IPBS software can enable used to: (1) interoperate within an array of medical equipment typical of acute care, and (2) automate feedback/alert systems for clinical care protocols. The specialized software may provide automation and feedback methods consistent with and customized to the existing flow of care of the participating healthcare institution. Through the application of a feasible engineering solution, the clinical informatics of the IPBS serves to provide clinical value and promote, rather than technically burden, the operational workflows within the healthcare environment.

Figure 6:
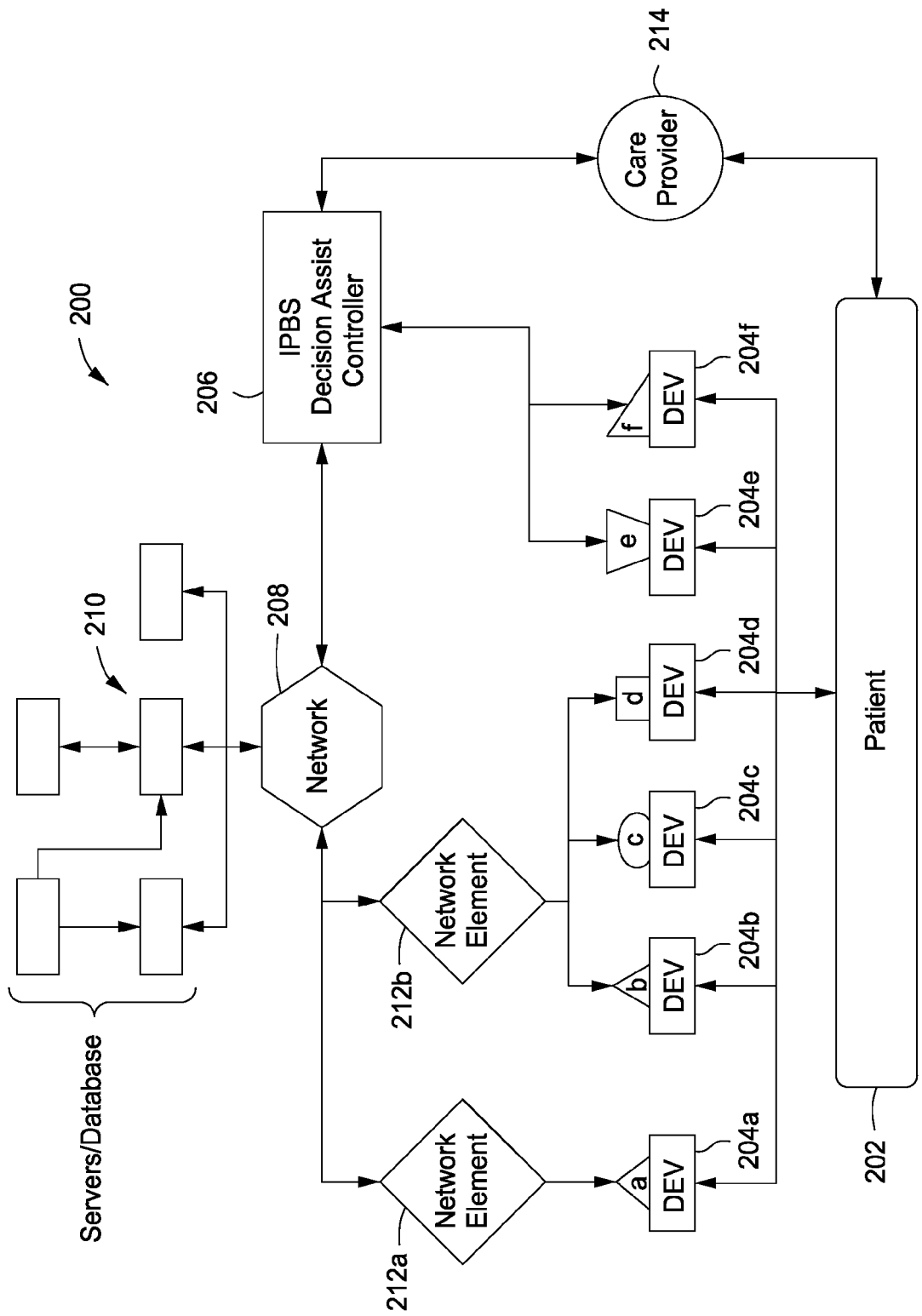
FIG. 6 shows one embodiment of an integrated patient bed system architecture of the present invention.

FIG. 6 shows one embodiment of an integrated patient bed system architecture 200 of the present invention. A patient 202 is connected to a variety of medical devices 204a-f. In present applications the data obtained from the devices is made available to users in a uni-direction manner, that is, the devices 204a-f provide information but are not controllable to deliver patient case. These devices 204a-f can use any of a variety of data exchange methods, including wired or wireless, and can exchange data or commands between any device and network element or directly with the IPBS Decision Assist Controller 206. Examples of devices 204a-f include, but are not limited to any device capable of assessing data related to patient care status or effecting an action related to patient care including, but not limited to, administration, communication, patient movement, transport, monitoring, diagnosis, treatment, or resuscitation. The controller 206 provides information to a network 208 or can be displayed for providing information to a care provider 214. The network 208 can be in communication with local or remote servers that include patient information (e.g., clinical history, pre-existing conditions, vaccinations, billing history, insurance, x-rays, MRIs, hematology). Taking patient care a step further, the care provider 214 can direct the controller to then access and direct the action of the medical devices to the patient using network elements that are able to provide input to the devices.

Figure 7:
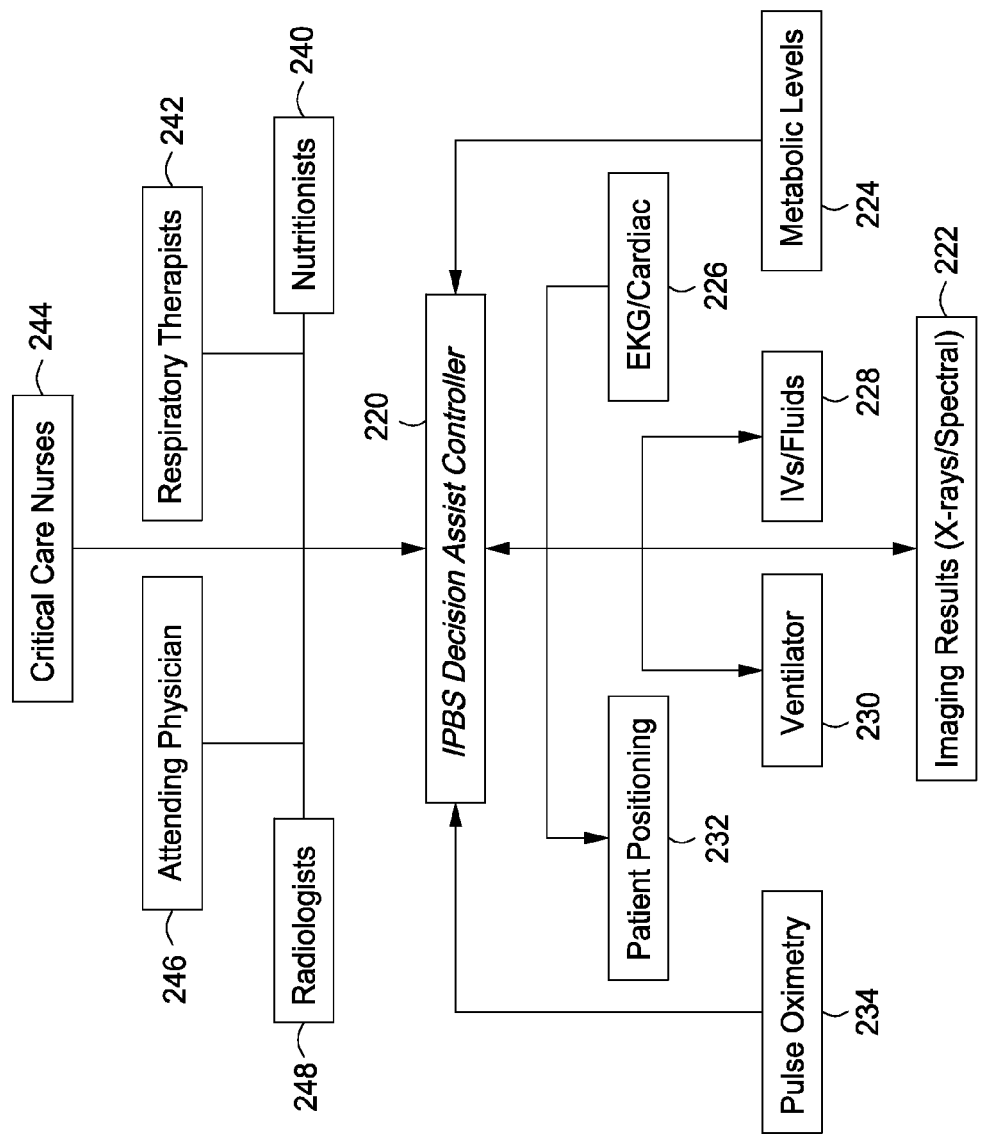
FIG. 7 shows a flow diagram of the basic integrated patient bed system controller architecture.

FIG. 7 shows a flow diagram of the basic integrated patient bed system controller architecture and its relationship with clinical informatics system flow. Referring to FIG. 7, a central controller, computer or CPU 220 serves as the hub of communication within instruments and between healthcare professionals and the patient. The CPU 220 acts as a relay center to enable communication between instruments. For example, when conducting an x-ray 222 of the patient's arm, the patient positioning system 232 will ensure that the patient is appropriately situated within the bed at which point the computer will initiate the x-ray equipment. While intercommunication is critical to the success of the IPBS, the present invention enables communication of patient data to various healthcare providers and the subsequent automation of clinical protocols. For example, if the system determines that the patient movement within the bed and breathing patterns no longer emulate that of a sleeping patient given inputs from pulse oximetry 234, ventilator 230, EKG/Cardiac 226 or metabolic levels 224, then one or more of the health care providers 240-248 are alerted based on the preset or customized reporting data input with the CPU 220. The CPU 220 will prompt a change in ventilator 230 settings to adjust to the breathing characteristic of the awakened state. The critical care nurse 224 on duty will then be alerted of the alteration and prompted to ensure that appropriate adjustments were made and to offer direct patient care assistance.

Preventing pressure ulcers involves redistribution of pressure away from bony prominences on the patient and maintenance of a clean, dry environment. Currently, no standardized care protocol has been defined for ulcer prevention, nurses are simply directed to move the patient every two hours and check the patient's skin for signs of breakdown. IPBS can be preprogrammed with code segments that enable specific clinical protocols based on the risk level of the patient determined by, e.g., the Braden scale. For example, if the patient is deemed high risk by the nurse; the central computer station will provide a checklist for the nurse during rounds (i.e. reminders to change the linen sheets, provide water for the patient, and a skin check). As IPBS also enables intelligent mechanical positioning, in which case the software enables the bed to readjust the patient's position to avoid, e.g., high-pressure points, heat or cool the skin, increase or decrease humidity at the skin surface or even change the temperature/environment settings of the patient's immediate surrounding (within the immediate patient's envelope) or of the entire room. Movement protocols can be preset or vary based on sensor data obtained from the electromagnetic wave detection system that queries the tissue between the patient and the support (e.g., the patient bed) or based on the input from sensor placed on the patient at or about suspected locations that need scrutiny to eliminate or prevent bed sores. Furthermore, a patient pressure map analysis and clinical studies can be conducted by healthcare professionals prior to patient admission to ascertain tissue health prior to initiating treatment. Using the present invention, a patient's tissue health can be documented prior to admission for purposes of medical reimbursement for patient care. The present invention also increases monitoring and provides critical checks and balances that help increase the clinical applicability and efficacy of a variety of manual, semi-automated and automated decisions.

The present invention also allows monitoring and data gathering and Input/Output tracking of, e.g., all fluids that enter and exit the patient. Fluids monitored within the critical care environment typically include urine output, drugs administered, nutritional feedings, gastric/nasal drainage, and chest drainage. Tracking such values ensures the appropriate hydration and nutritional intake of the patient that would be of value, not only to the nutritionist—but the attending physician as well. Issues such as urine retention and excessive chest drainage are critical for the assessment of other problems potentially related to surgical issues, medication management, and underlying physiological problems. Beyond the value added to clinical outcomes, the automation of fluid tracking greatly reduces the administrative responsibilities and chances of error for critical care nurses.

Ventilator management is a critical area of improvement in preventing prolonged intubation, ventilator associated pneumonia, and maintaining the patient's natural lung function.

By enabling software to detect subtle changes in a patient's respiratory and cardiac trends, recommendations can be made to the healthcare personnel to alter ventilator settings. A key consideration in developing such software is the understanding that the data must be contextualized to the patient environment. For example, if a tube has been disconnected, the flat-line reading would not be directly linked to a physiological issue. It is critical that the intelligence system implemented prevent false positives through algorithms such as that described in FIG. 8.

Figure 8:
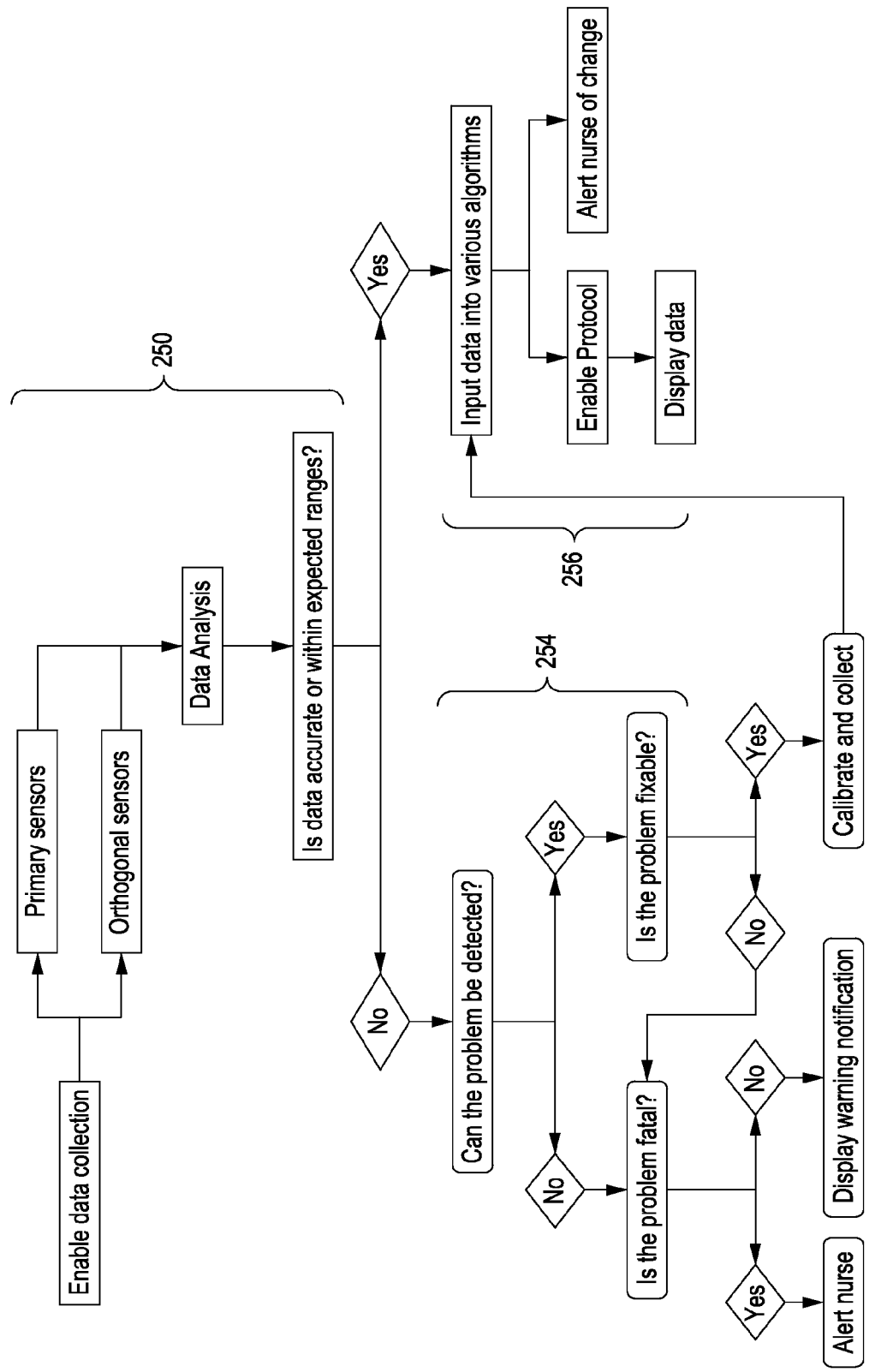
FIG. 8 shows a detailed flow diagram of the basic integrated patient bed system controller architecture.

FIG. 8 shows a detailed flow diagram of the basic integrated patient bed system controller architecture. In the flow diagram steps 250, basic patient data is gathered and stored from a variety of sensors (primary and orthogonal) and the data is analyzed to determine if the data is within the expected range (e.g., blood $O_2$). Next, a decision tree is reached in which the system determines whether there is a problem with the equipment in flow 254. In flow 256 a check and balance on the data is provide in that the data that appears correct is nevertheless analyzed and if necessary the health care professional is contacted. If the data is out of range, then the system determines if it can provide the required correction (e.g., increase the rate of a ventilator) or if a medical professional should be alerted. If the problem cannot be corrected that is within the IPBS permissible corrective action, then the system still determined if a correction occurred or if a medical professional should still be contacted.

The IPBS architecture allows for customization and revision of based on local input from healthcare providers. For example, various medical treatment policies and procedures and be input into the system to determine which protocols to follow when providing care. These protocols can be provided as a preset design specification based on ideal system responses and alerting systems. Essentially, the central computing station within the patient room provides intelligent assistance to the healthcare provider by enabling existing engineering tools.

Figure 9:
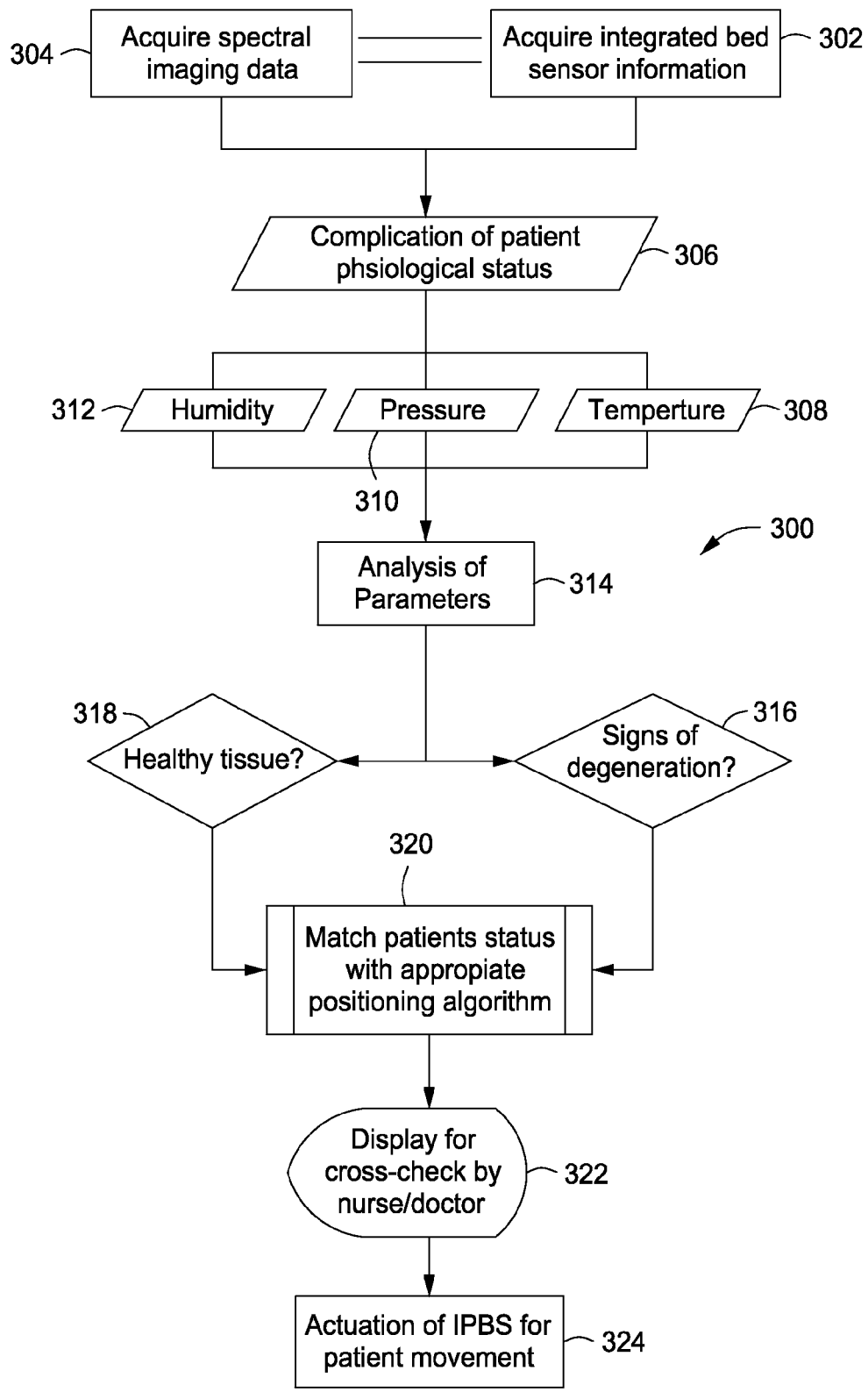
FIG. 9 is a flow diagram that correlates the tissue health image detection with the basic integrated patient bed system controller.

FIG. 9 is a flow diagram that correlates data from the tissue health image detection with the basic integrated patient bed system controller. In this example, the patient positioning flow 300 begins with the acquisition of patient spectral data from a current and/or prior scan 302, 304. Next, a compilation 306 is conducted of the patient's physiological status, e.g., upon patient intake to provide documentation of any pre-existing conditions, trauma and the like. Next, the system determines various environmental that can affect tissue health, e.g., temperature 308, pressure 310 or humidity 312. The IPBS then analyses the parameters 314 and identifies regions of the patient's tissue that may be showing signs of stress, fatigue or degeneration 316 and those portions that are healthy 318. Next, the IPBS matches the portions of health and potentially non-healthy tissue of the patient's tissue health with the patient's position on the patient support system and runs a positioning algorithm that maps likely weight, pressure, sheer, temperature, humidity, blood, tissue and skin oxygen levels and other conditions (e.g., diabetes, body temperature or dehydration) to determine the best position for the patient. Next, the proposed positioning is displayed 322 for the health care professional to accept, reject or place on automatic the patient positioning system. Finally, at step 324 the bed is directed to change the environmental parameters (bed position, pressure, temperature, humidity, change in linens) at the location of patient contact with the bed.

Figure 10A:
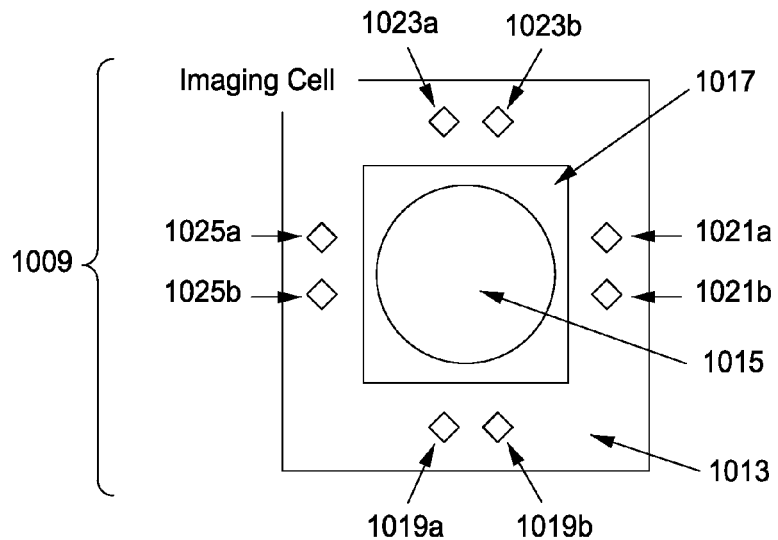
FIG. 10A shows the top view of an imaging cell, comprising a light source (one or more light emitting diodes), a lens, an imaging chip, and a PCB for providing mechanical and electrical support on which the imaging chip is mounted.

FIG. 10A is a representation of an imaging cell 1009. Imaging cell 1009, has an imaging chip 1017, that comprises a lens 1015. The imaging chip is surrounded by light sources or LEDs, 1019a, 1019b, 1021a, 1021b, 1023a, 1023b, 1025a, and 1025b. The imaging chip 1017, and the LEDs, 1019a, 1019b, 1021a, 1021b, 1023a, 1023b, 1025a, and 1025b are mounted on a printed circuit board (PCB) 1013. Furthermore, a digital signal processor and memory may be incorporated on each PCB to facilitate local signal processing and reduce the amount of data sent to a remote computer)

Figure 10B:
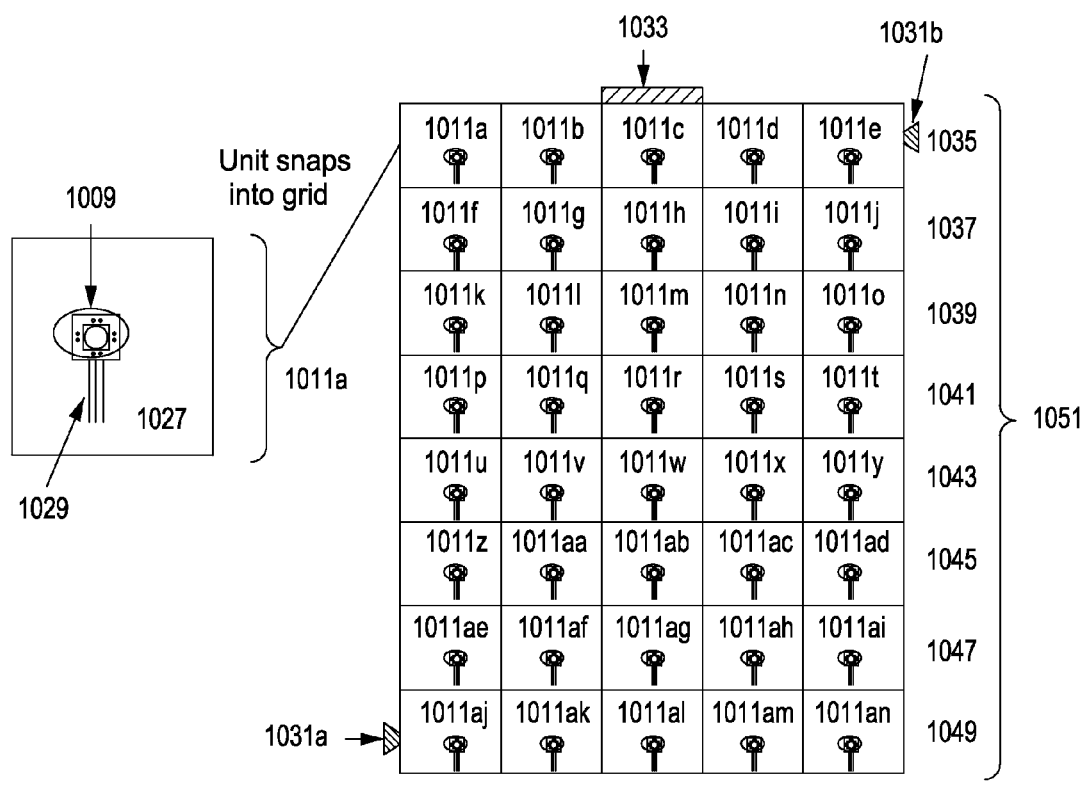
FIG. 10B depicts a 5×8 imager array with electrical and PC connections. The imager array has 40 imaging units, snapped on to the grid surface.

FIG. 10B is a diagram of an imaging super-array 1051 (the number of total units required is a function of the application). Super-array 1051 as shown in FIG. 1B is 5×8 grid comprising of 40 units (11a-11an). Each unit comprises of an imaging cell similar to 1009 (as described in FIG. 10A), mounted on a mechanical support 1027 and has electrical contacts 1029 at the back. The back of each imaging cell unit (for e.g. 1011a) snaps into the grid of the super array 1051. The signal from the super-array is transmitted from each individual grid to the PC via standard connections 1031a and 1031b located on the grid. In addition to the PC connection, outlet power 1033 is available on both sides of the grid to maintain flexibility in the patient environment. The arrangement of each unit within the grid is also flexible (the number of units and spatial relationship can be altered according to the needs of the patient). The super-array grid 1051, described in FIG. 10B has forty units distributed over eight rows 35, 37, 39, 41, 43, 45, 47, and 49. Row 35 has units 1011a, 1011b, 1011c, 1011d, and 1011e. Row 37 has units 1011f, 1011g, 1011h, 1011i, and 1011j. Row 39 has units 1011k, 1011l, 1011m, 1011n, and 1011o. Row 41 has units 1011p, 1011q, 1011r, 1011s, and 1011t. Row 43 has units 1011u, 1011v, 1011w, 1011x, and 1011y. Row 45 has units 1011z, 1011aa, 1011ab, 1011ac, and 1011ad. Row 47 has units 1001ae, 1011af, 1011ag, 1011ah, and 1011ai. Finally, row 49 has units 1011aj, 1011ak, 1011al, 1011am, and 1101an.

Figure 10C:
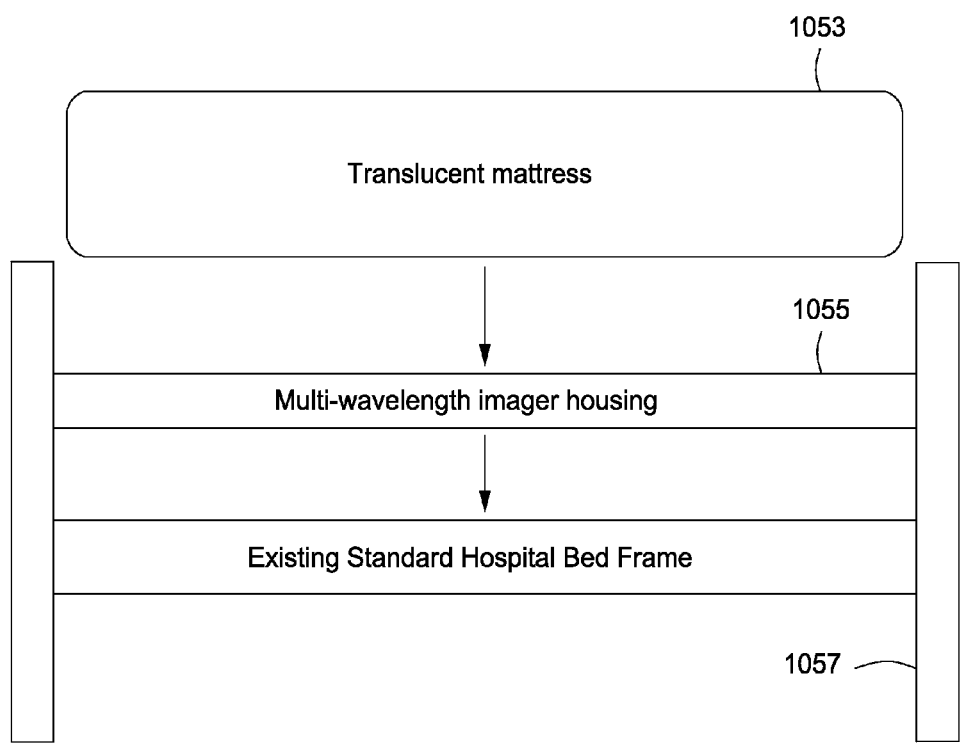
FIG. 10C shows an image of an imager array/housing that is integrated with a standard hospital bed.

The housing may conform to the standard hospital bed sizes used in current health care environments, thus allowing for the immediate use of such technologies. FIG. 10C represents the application of the present invention in a hospital/clinical setting. The housing 1055 is simply placed on the bed frame 1057, beneath the mattress 1053 prior to the transfer of the patient onto that bed. From there, all access points required for the utilization of the imager 1055 would be located on the side of the array allowing easy access for nurses and physicians.

Figure 11A:
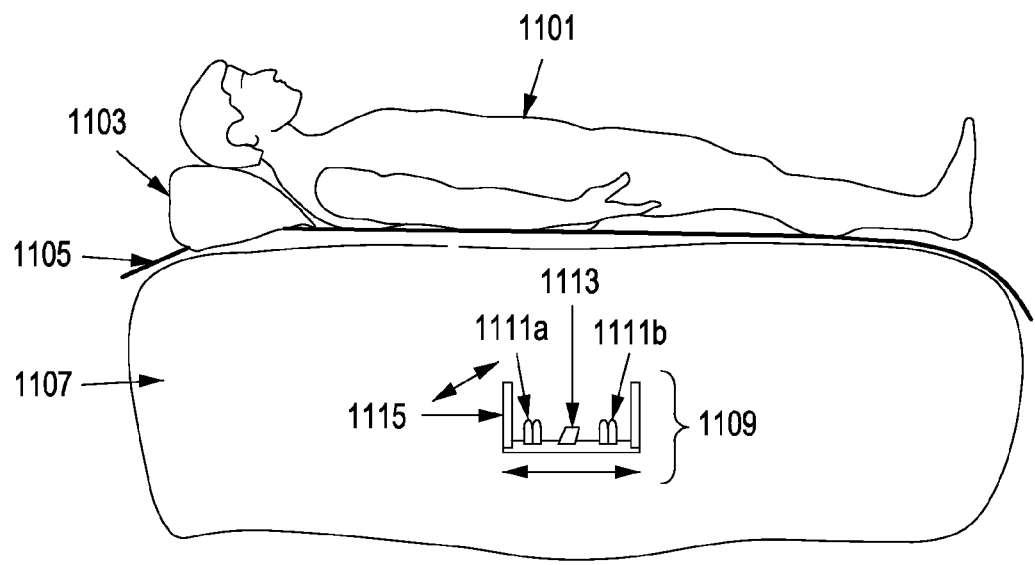
FIG. 11A shows an image of a mattress with a module. The patient is on the bed in the laying down position, and the imaging apparatus can move on a x-y stage.

FIGS. 11A-11L show different arrangements and designs of the imaging device of the present invention in different hospital settings. FIG. 11A shows an image of a mattress 1107 with an embedded module 1109. The patient 1101 is on the bed in the laying down position, with a pillow 1103 and a sheet 1105 (non-target). The module 1109 comprises a solid support 1115, two light sources 1111a and 1111b, and a detector 1113 all attached to the solid support 1115. The imaging apparatus 1109 of the present invention is capable of movement on a x-y stage.

Once the module is placed within the mattress movement on a x-y stage or a x-y-z stage would typically occur automatically based upon a predetermined program or on preset criteria in order to provide a complete image of the areas of interest or images of specific areas. In certain cases there could be a feature that would allow an operator to move the module to a specific area manually. Once information is obtained from the analysis of the imaging data that determines that the patient should be repositioned, the repositioning can be achieved by: (i) alerting clinical staff as to the location(s) of problem areas so that the course of repositioning may be determined, or (ii) by changing pressure(s) within the mattress or other properties of the mattress either automatically or manually, or (iii) by changing the position(s) of the bed and frame either automatically or manually.

Figure 11B:
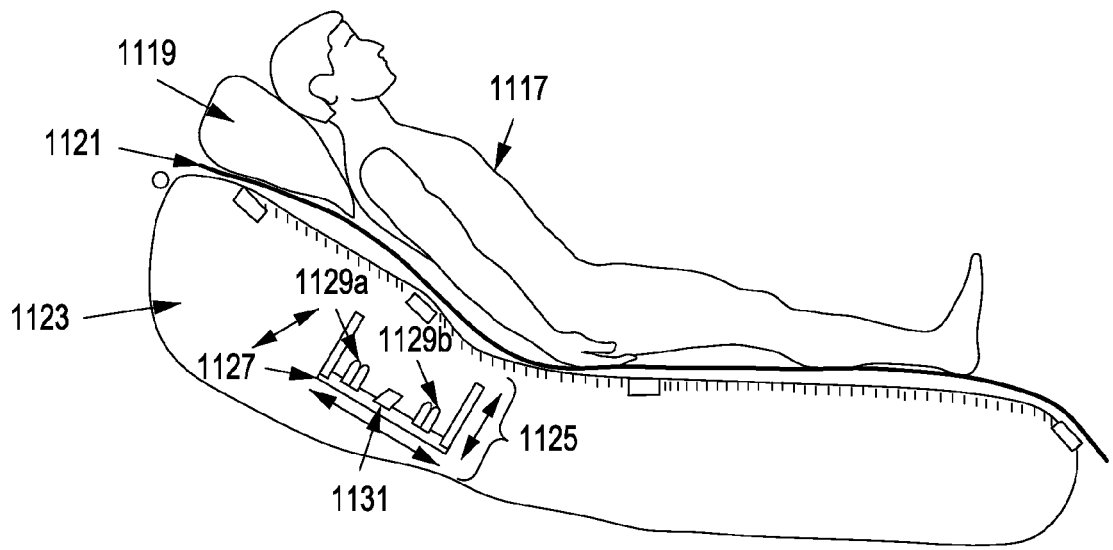
FIG. 11B shows an image of a mattress with a module. The patient is on the bed in the sitting up position, and the imaging apparatus can move on a x-y-z stage

FIG. 11B shows an image of a mattress 1123 with an embedded module 1125. The patient 1117 is on the bed in the sitting up position, with a pillow 1119 and a sheet 1121 (non-target). The module 1125 comprises a solid support 1127, two light sources 1129a and 1129b, and a detector 1131 all attached to the solid support 1127. The imaging apparatus 1125 of the present invention can move on a x-y-z stage.

Figure 11C:
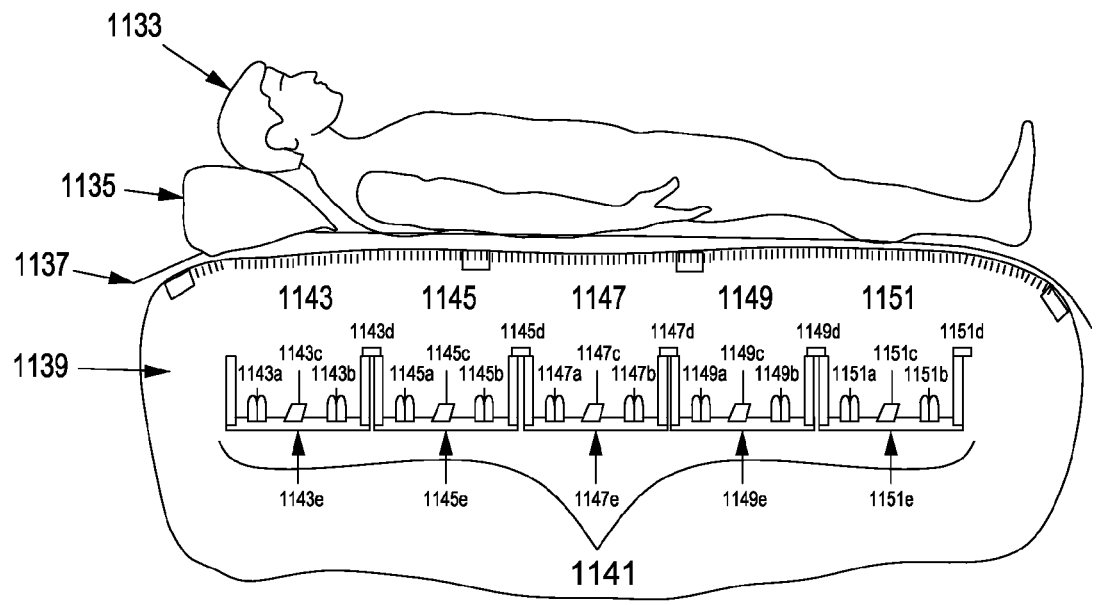
FIG. 11C shows an image of a mattress with a super array module. The patient is on the bed in the laying down position.

FIG. 11C shows an image of a mattress 1139 with a super array module 1141. The patient 1133 is on the bed in the laying down position with a pillow 1135 and a sheet 1137 (non-target). The super array module comprises of five units, 1143, 1145, 1147, 1149, and 1151. Each unit comprises two light sources, a detector, a solid support, and a connector connecting the adjacent units. Unit 1143 has light sources 1143a and 1143b, a detector 1143c, and a support 1143e. Connector 1143d connects unit 1143 with unit 1145. Unit 1145 has light sources 1145a and 1145b, a detector 1145c, and a support 1145e. Connector 1145d connects unit 1145 with unit 1147. Unit 1147 has light sources 1147a and 1147b, a detector 1147c, and a support 1147e. Connector 1147d connects unit 1147 with unit 1149. Unit 1149 has light sources 1149a and 1149b, a detector 1149c, and a support 1149e. Connector 1149d connects unit 1149 with unit 1151. Unit 1151 has light sources 1151a and 1151b, a detector 1151c, and a support 1151e. Connector 1151d is free to connect with any additional units that may be attached to the super array module.

Figure 11D:
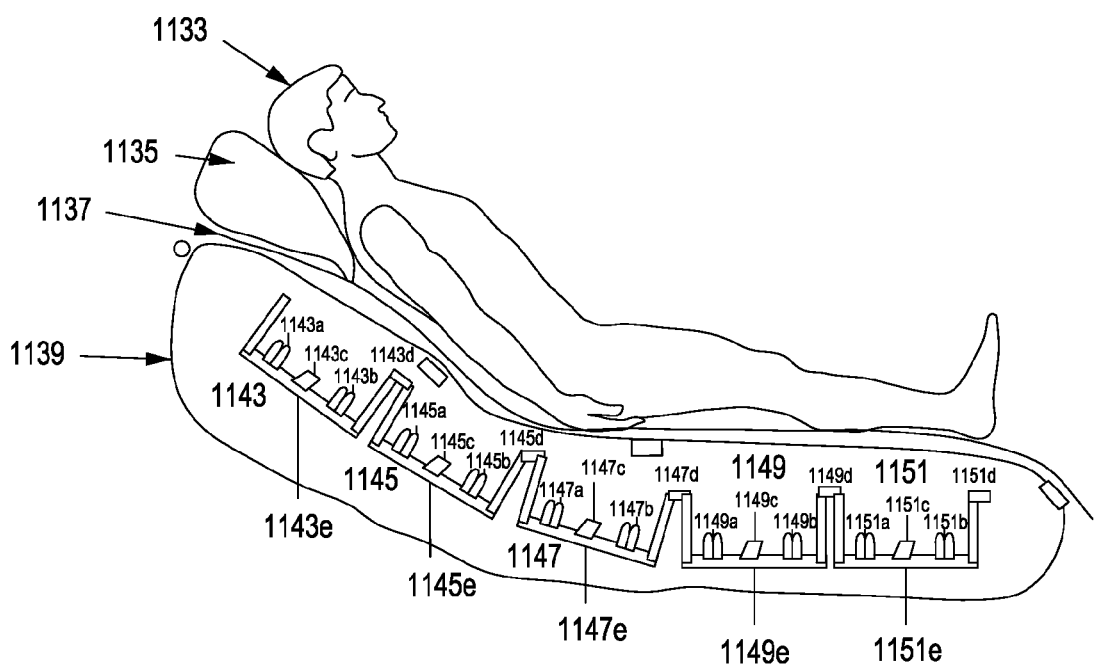
FIG. 11D shows an image of a mattress with a super array of modules. The patient is on the bed in the sitting up position, and the super array of modules is flexibly connected.

FIG. 11D is similar to FIG. 11C with the exception that the patient 1133 is on the bed in the sitting up position, and the super array of modules 1141 is flexibly connected. The patient 1133 is on the bed in the sitting up position with a pillow 1135 and a sheet 1137 (non-target). The super array module comprises of five units, 1143, 1145, 1147, 1149, and 1151. Each unit comprises two light sources, a detector, a solid support, and a connector connecting the adjacent units. Unit 1143 has light sources 1143a and 1143b, a detector 1143c, and a support 1143e. Connector 1143d connects unit 1143 with unit 1145. Unit 1145 has light sources 1145a and 1145b, a detector 1145c, and a support 1145e. Connector 1145d connects unit 1145 with unit 1147. Unit 1147 has light sources 1147a and 1147b, a detector 1147c, and a support 1147e. Connector 1147d connects unit 1147 with unit 1149. Unit 1149 has light sources 1149a and 1149b, a detector 1149c, and a support 1149e. Connector 1149d connects unit 1149 with unit 1151. Unit 1151 has light sources 1151a and 1151b, a detector 1151c, and a support 1151e. Connector 1151d is free to connect with any additional units that may be attached to the super array 1141.

Figure 11E:
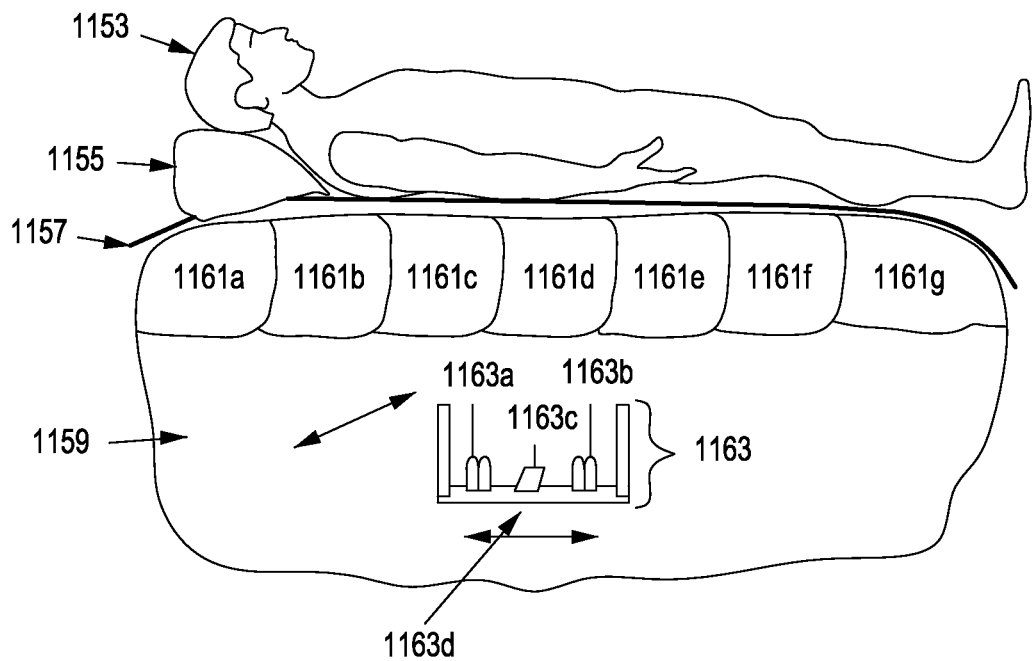
FIG. 11E shows an image of a mattress, patient, and a module in the mattress. The patient is on the bed in the laying down position, with chambers to control individual pressures. The chambers are shown with the moving apparatus, but they can be present with any configuration of modules

FIG. 11E shows an image of a mattress 1159, patient 1153, with a pillow 1155, sheet 1157 (non-target) and a module 1163 in the mattress. The patient 1153 is on the bed in the laying down position, with chambers 1161a-1161g to control individual pressures. The imaging apparatus 1163 can move on a x-y-z stage, and has light sources 1163a and 1163b, detector 1163c and a support 1163d. The chambers 1161a-1161g are shown with the moving apparatus 1163, but they can be present with any configuration of modules.

Figure 11F:
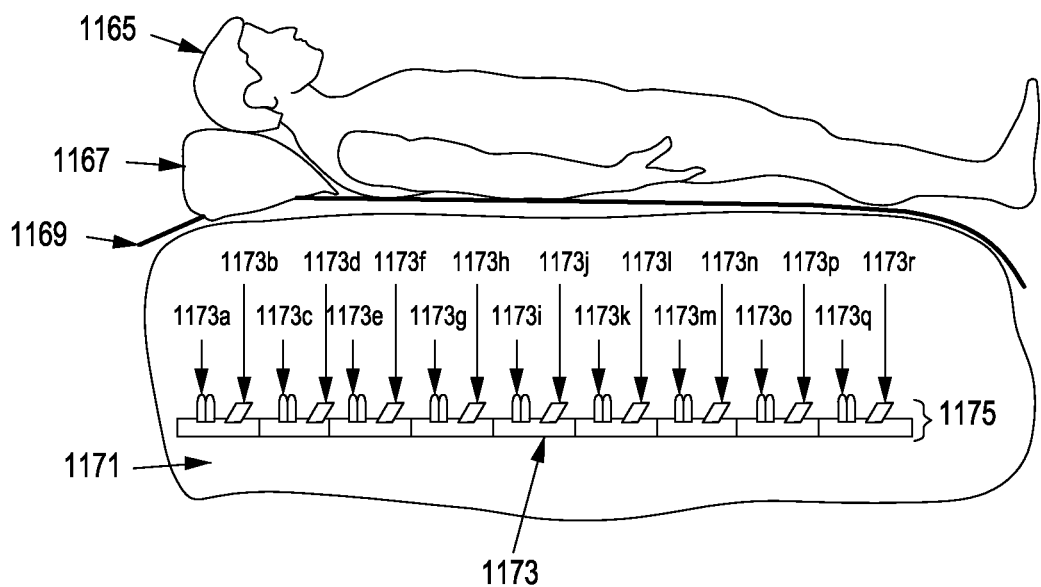
FIG. 11F shows an image of a mattress, module in the mattress, and a patient in the laying down position. The imaging apparatus is comprised of a large substrate

FIG. 11F represents a mattress 1171, and a module 1175 embedded in the mattress, the patient 1165 with a pillow 1167 and sheet 1169 (non-target) is in the laying down position. The imaging apparatus 1175 is comprised of a large substrate 1173, having light sources 1173a, 1173c, 1173e, 1173g, 1173i, 1173k, 1173m, 1173o, and 1177q and detection units 1173b, 1173d, 1173f, 1173h, 1173j, 1173l, 1173n, 1173p, and 1173r attached to it.

Figure 11G:
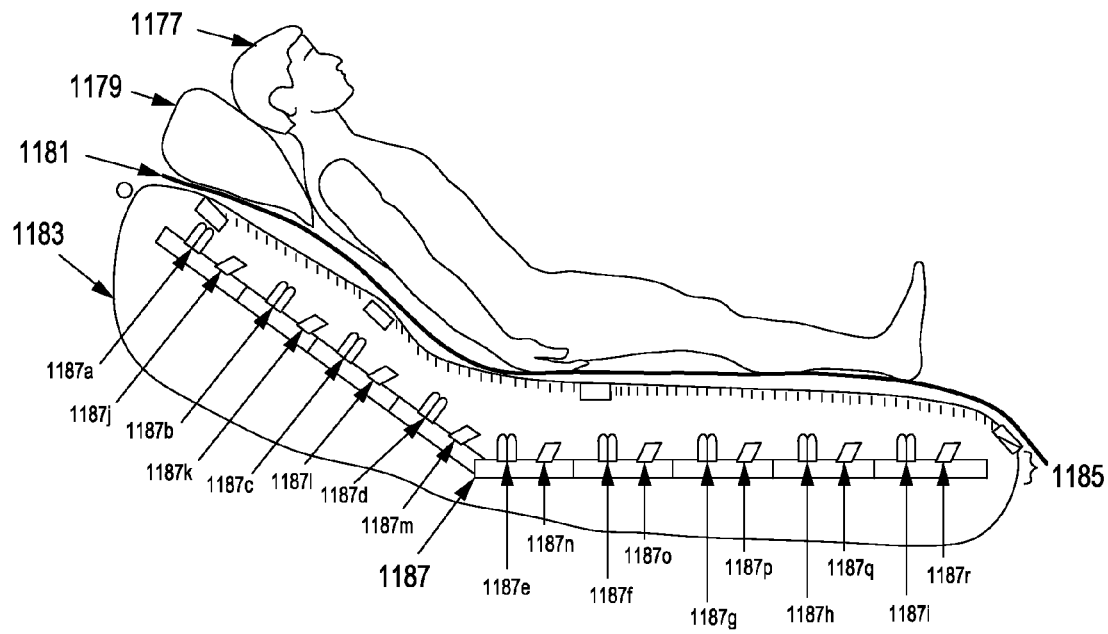
FIG. 11G shows an image of a mattress, a patient in the sitting up position, and a module in the mattress. The imaging apparatus comprised of large flexible substrate

FIG. 11G shows an image of a mattress 1183, a patient 1177 in the sitting up position with a pillow 1179, sheet 1181 (non-target), and a module 1185 in the mattress. The imaging apparatus 1185 is comprised of large flexible substrate 1187, with light sources 1187a-1187i and detectors 1187j-1187r attached to it.

Figure 11H:
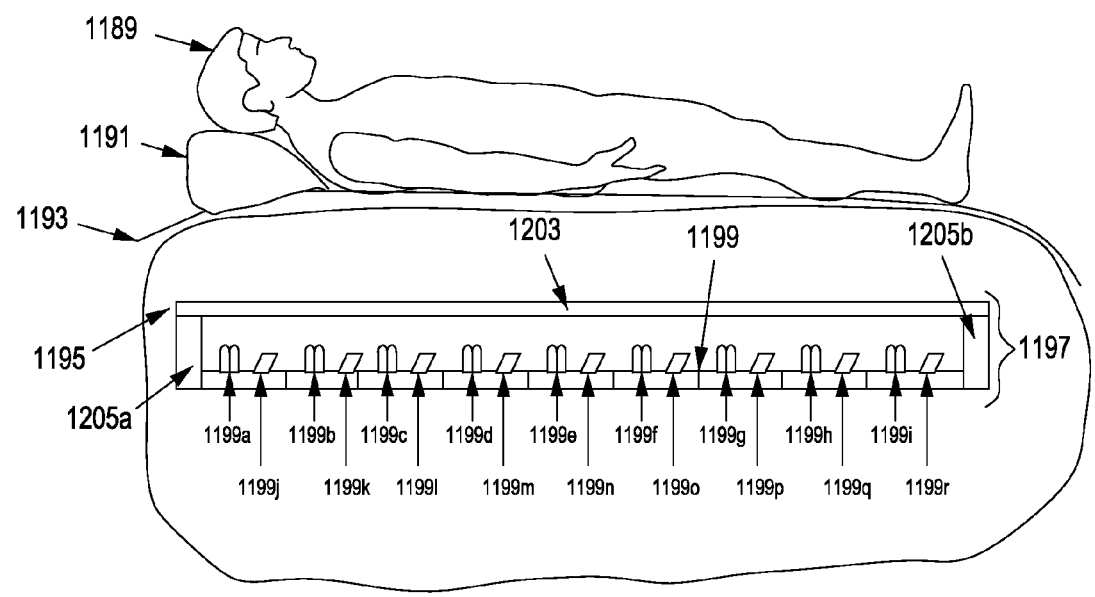
FIG. 11H shows an image of a mattress, a patient in the laying down position, and a module in the mattress. The imaging apparatus is comprised of large substrate showing intermediate CPR support structure (window, mesh, etc.).

FIG. 11H shows an image of a mattress 1195, a patient 1189 in the laying down position with a pillow 1191, sheet 1193 (non-target), and a module 1197 in the mattress. The imaging apparatus 1197 is comprised of large substrate 1199 showing intermediate CPR support structure including a window 1201, a mesh 1203, and a supporting frame 1205. The substrate 1199 has light sources 1199a-1199i and detectors 1199j-1199r attached to it.

The module base support comprises a hard outer material for the casing, which is likely to be a plastic or metal. Any material that can provide a stiff support could be used for this purpose. A Printed Circuit Board (PCB) would be affixed to the inside of the outer module casing. The PCB would likely be made of FR-4, which is an industry standard abbreviation for Flame Retardant 4. The LEDs and detectors come in industry standard packages that are attached to the PCB using methods well known in the art. Small wedges can be place in between the LEDs and the PCB in order to orient the LED at an angle that is not at 90% to the plane of the PCB. The module itself is either physically attached to the movement mechanism of the x-y or x-y-z stage, for example but not limited to the case of a scanning configuration. In the case of the super array, whereby modules are attached together, the flexibility is obtained by securing the modules to one another on a single plane, so as to allow for motion in response to changes in Z.

Figure 11I:
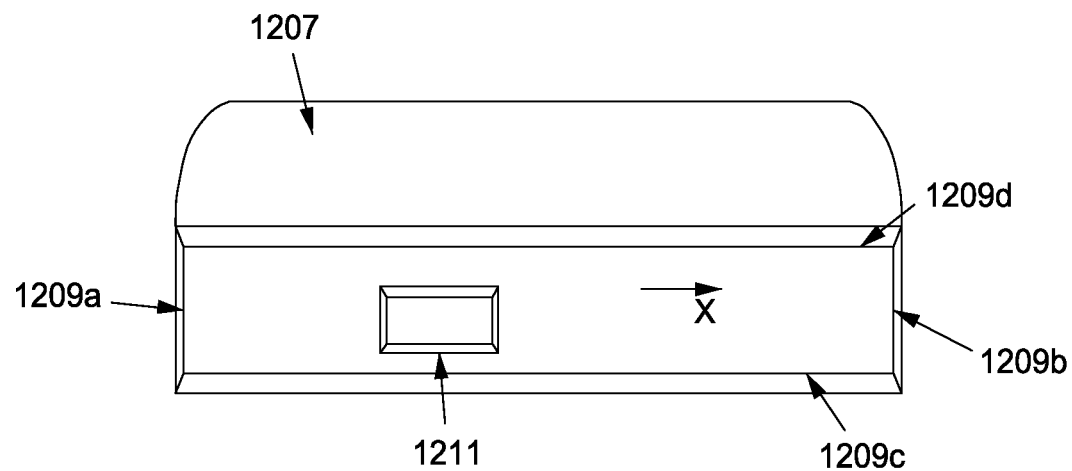
FIG. 11I shows an image of an airtight mattress and frame with a module in the mattress. The module is capable of movement on a x-y stage.
Figure 11J:
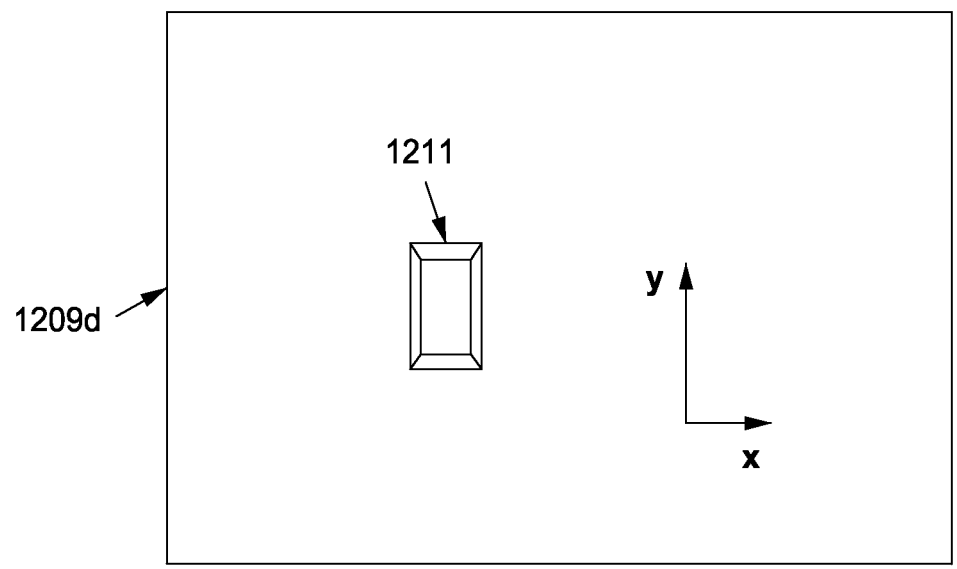
FIG. 11J is a top view of the image described in 11I.
Figure 11K:
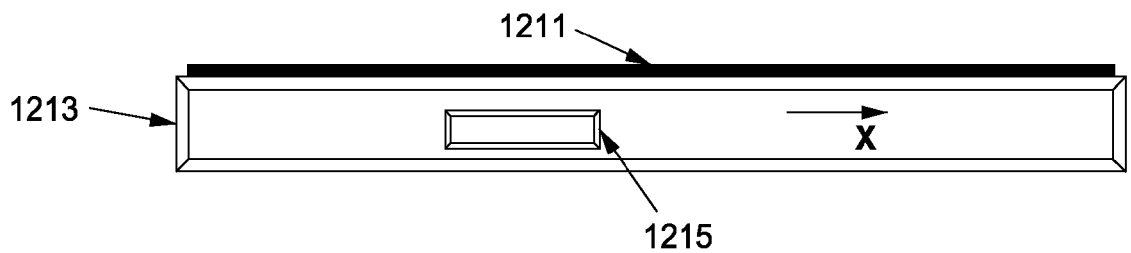
FIG. 11K shows an x-y stage frame with top attachable surface shown in horizontal orientation so that a person may lay atop the surface.
Figure 11L:
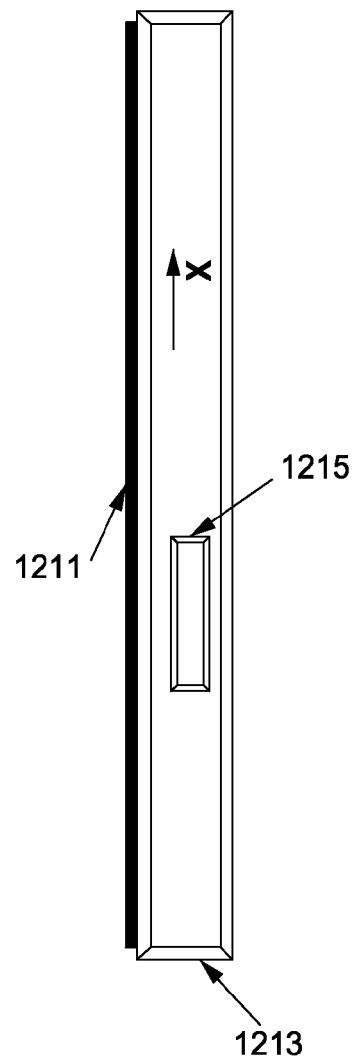
FIG. 11L shows the x-y stage frame with top attachable surface shown in vertical orientation so that a person may stand or otherwise be positioned adjacent to the surface in a vertical position.

FIG. 11I shows an image of an airtight mattress 1207 and frame 1209 with a module 1211 in the mattress. The module 1211 is capable of movement on a x-y stage. FIG. 111J is a top view of the image described in 1011I, comprising a mattress 1207, a frame 1209 and a module 1211. FIG. 11K shows an x-y stage frame with top attachable surface shown in horizontal orientation so that a person may lay atop the surface. The surface may be rigid (e.g. glass or plexiglass) or made of non-rigid materials (e.g. cloth or pliable plastic). FIG. 11L shows the x-y stage frame with top attachable surface shown in vertical orientation so that a person may stand or otherwise be positioned adjacent to the surface in a vertical position. The surface may be rigid (e.g. glass or plexiglass) or made of non-rigid materials (e.g. cloth or pliable plastic). The frame may be placed onto a support structure that may vary the orientation at any angle between vertical and horizontal, in this way varying the pressure applied to the person.

Figure 12A:
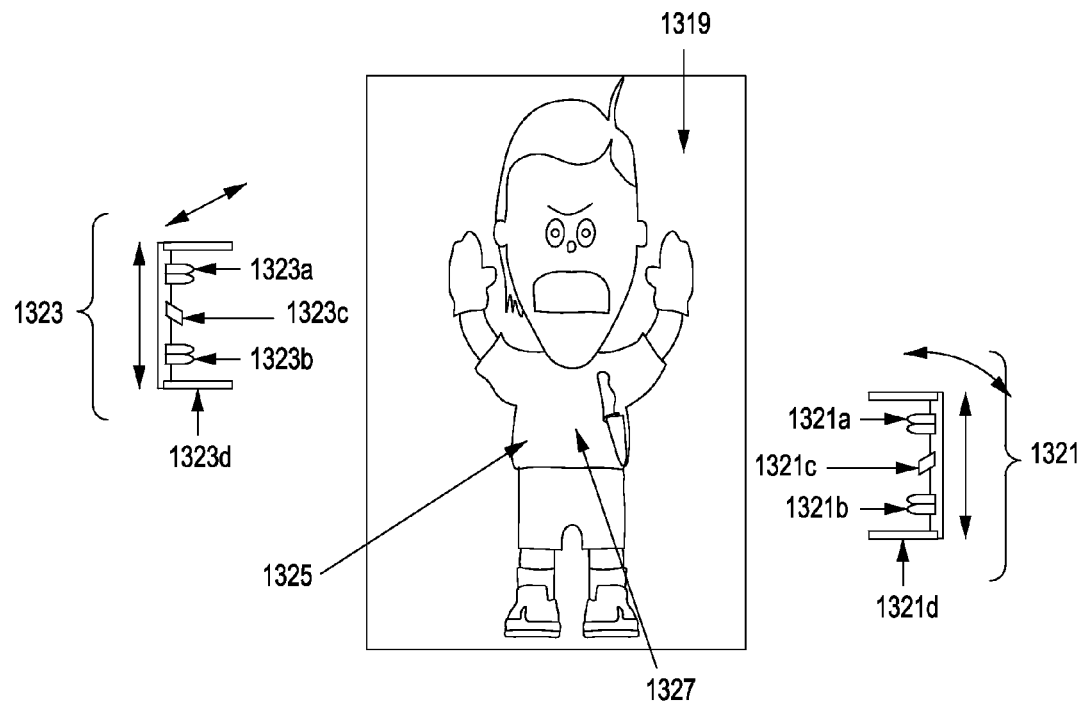
FIG. 12A is an image of an airport scanner/detector having single modules capable of being orientated on a x-y translation stage and curved translation stage for detection of subjects carrying concealed body weapons.

FIG. 12A is an image of an airport scanner/detector 1319 having two single modules 1321 and 1323 capable of being orientated on a x-y translation stage and curved translation stage for detection of a subject 1325 carrying a concealed body weapon 1327. The module 1321 has a base 1321d, two light sources 1321a and 1321b and a detector 1321c. The module 1323 has a base 1323d, two light sources 1323a and 1323b and a detector 1323c.

Figure 12B:
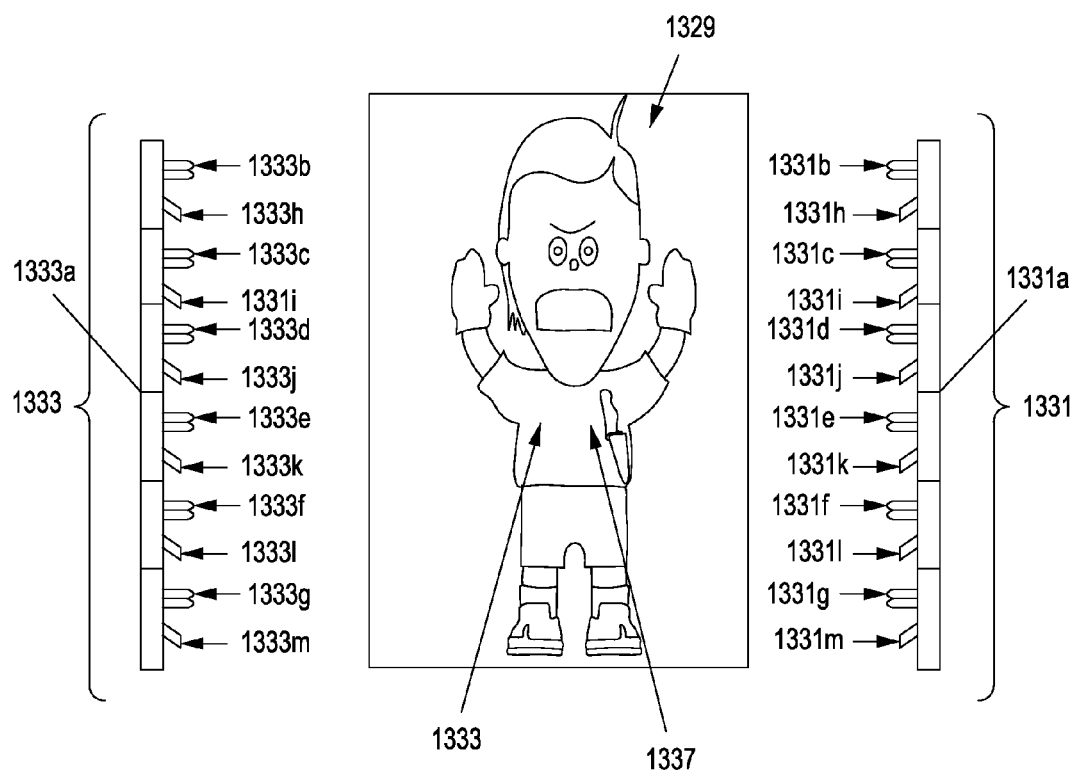
FIG. 12B is an image of an airport scanner/detector having strips of modules (light sources and detectors) for detection of subjects carrying concealed body weapons.

FIG. 12B is an image of an airport scanner/detector 1329 having two strips of modules 1331 and 1333 (light sources and detectors) for detection of a subject 1335 carrying a concealed body weapon 1337. Module strip 1331 has a base 1331a, light sources 1331b-1331g and detectors 1331h-1331m. Module strip 1333 has a base 1333a, light sources 1333b-1333g and detectors 1333h-1333m.

In order to record the time variations of the captured spatial images at time scales fast enough to observe dynamic behaviors that result from the beating heart or pulsatile blood flow it is necessary to record many samples each second for the various wavelengths and lighting conditions. As such it is necessary to provide electronics that allow for the rapid control of the lighting conditions. As an example, for the case where two wavelengths are desired and the illumination properties may be achieved by using LEDs, a simple circuit may be constructed to provide for driving of multiple LEDs of each type whereby the particular wavelength of LEDs that is turned on is determined by the sign of the power supply and whereby the background condition may be affected when the power supply bias is zero.

Figure 13A:
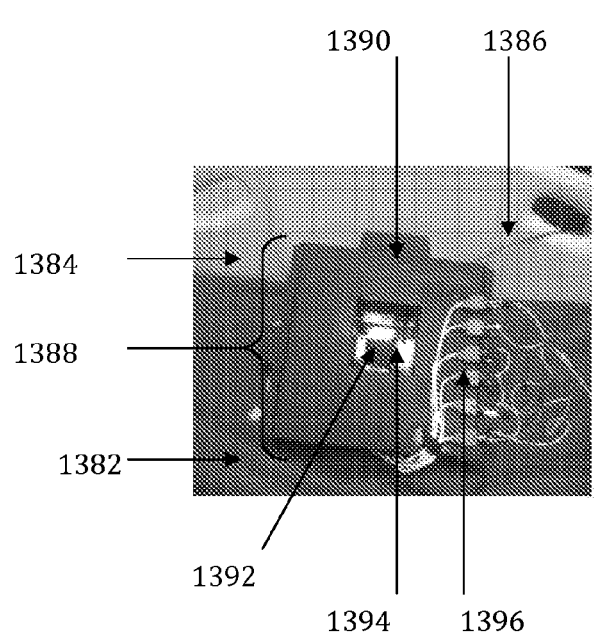
FIG. 13A depicts a prototype module shown with Red LEDs switched on (660 nm), in an absorbing box enclosure and wired interconnects.

FIG. 13A shows a prototype of an imaging module 1388. Module 1388 is placed on a mattress 1382. The mattress 1382 is supported by bed frame 1384. The imaging module 1388 is enclosed in a hard shell 1390, has an imaging chip 1392, red LEDs (660 nm) 1394, and wired interconnects 1396. The module can be connected to any monitoring/recording device or is accessible to the nurses/physician by an access point 1386.

Figure 13B:
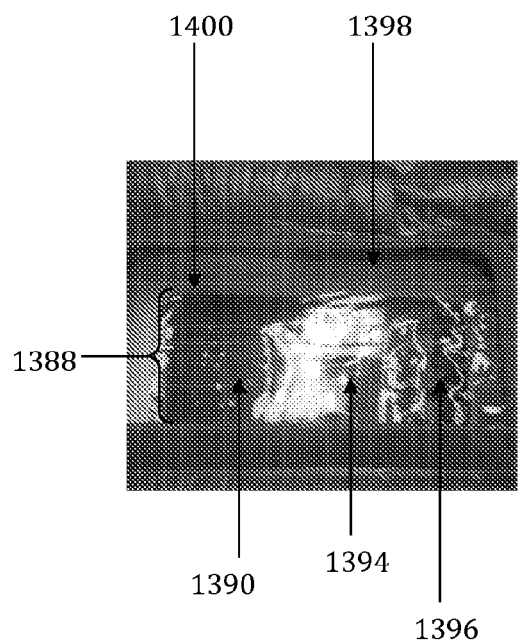
FIG. 13B shows the prototype module of FIG. 11A through a transparent air mattress with Red LEDs switched on (660 nm).

FIG. 13B depicts the imaging module 1388 of FIG. 13A, embedded in a transparent air mattress 1400, and having a transparent plastic case, 1398 at the top. The imaging module 1388 is enclosed in a hard shell 1390, has an imaging chip 1392, red LEDs (660 nm) 1394, and wired interconnects 1396.

Figure 13C:
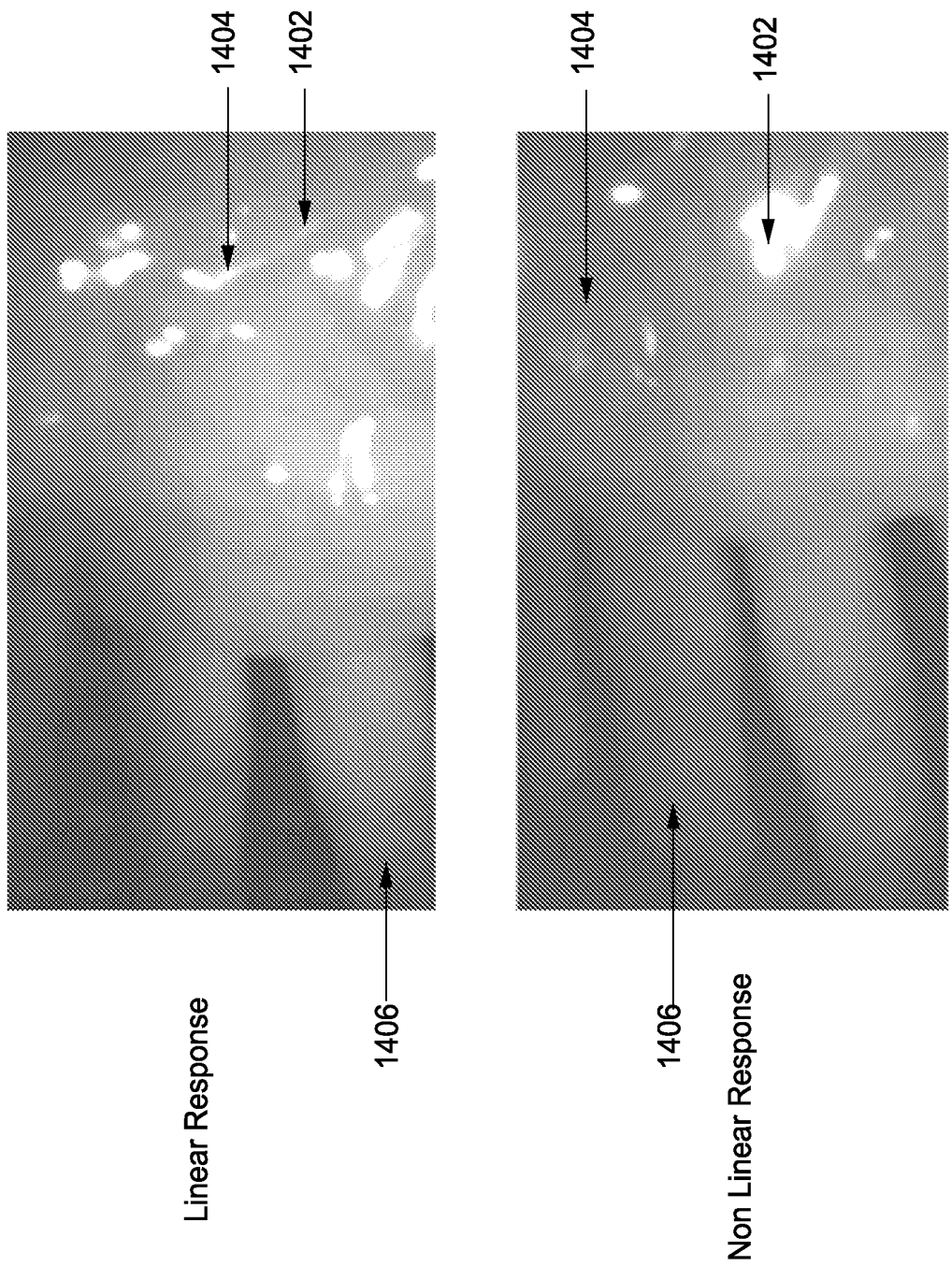
FIG. 13C shows the reduction of impact of specular reflection from a mattress surface through the use of non-linear detector response.

FIG. 13C shows a linear and a non-linear response obtained for a target (palm 1404 and fingers 1406) placed on a transparent plastic sheet or surface 1402. Imaging through a window gives rise to specular reflections where a portion of light from the source bounces from the window onto the detector, without going through the window and interacting with the patient. As discussed previously in the present invention, the first approach is to design the position and orientation of light sources selected to reduce or eliminate specular reflectance. The problem is further exacerbated when the window is a deformable plastic mattress surface, in which case the optimum positions and orientations of the light sources may be different for different deformations of the mattress. The present invention, solves the problem by considering the range of common deformations and selecting a superset of LED numbers, positions and orientations. Then during operation of the system, LEDs that cause significant specular reflections for a particular state of window are identified (as they tend to work to saturate the detectors) and turned off. The remaining LEDs continue to provide illumination of the desired area, but without producing significant specular reflections. With that said, in cases where creases form in the mattress it may not be possible to completely eliminate the specular reflections from these regions without significantly impacting the illumination of nearby regions. It is not expected that these types of reflections can be avoided by the position and orientation of the light sources. FIG. 13C depicts two images where creases in the mattress surface cause specular reflections indicated by the variety of bright spots. FIG. 13C (top) depicts the image as viewed by a CMOS imager where the output is proportional to the intensity of the detected light. FIG. 13C (bottom) depicts a similar image viewed by a CMOS imager where the output is not proportional to the intensity of light. Such a non-linear response serves to limit the areas around the creases that result in saturation of the detector as can be seen by the future number of specular reflection points in the image. This aspect is particularly important for integrated bed imaging to work, wherein there will be conditions where the dynamic range of the light in the scene is simply to large to be adequately imaged by an imager operating in a linear mode.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A patient support system comprising:
a patient support comprising one or more substrates;
an electromagnetic detector positioned to detect one or more parameters of a patient's tissue health, wherein the detector measures tissue in contact with or adjacent to the patient support;
a light source that emits waves;
wherein the electromagnetic detector detects wave reflections from the patient's tissue, wherein the wave emissions and reflections are selected to traverse the one or more substrates positioned between the electromagnetic detector and the patient's tissue; and
a processor connected to the detector that stores one or more parameters of the tissue's condition that are indicative of tissue health, wherein an indication of tissue health is used to change conditions at or about the site of tissue contact.

2. The system of claim 1, wherein the processor is connected to one or more support repositioning devices that automatically move the patient if a change in tissue health is detected.

3. The system of claim 1, wherein portions of tissue that show a change in tissue health are marked for continued monitoring.

4. The system of claim 1, wherein the processor is connected to one or more devices at the patient support that heat, cool, increase or decrease humidity, deliver pharmaceuticals, increase oxygen delivery, decrease pressure, increase pressure of the tissue at or about a site in need of treatment.

5. The system of claim 1, wherein the patient support comprises at least a portion of a hospital bed.

6. The system of claim 1, wherein the electromagnetic detector detects electromagnetic waves that are visible, infrared, near infrared or hyperspectral.

7. The system of claim 1, wherein the electromagnetic detector detects signals that the processor converts into at least one measurement of change in tissue conditions, wherein the at least one measurement is selected from tissue blood flow, tissue oxygenation, tissue temperature, tissue humidity, tissue compression, tissue shear or combinations thereof.

8. The system of claim 1, wherein the processor may further store additional patient data selected from age, gender, weight, patient blood pressure, tissue oxygenation, body temperature, humidity or combinations thereof over time to create one or more images of locations for therapy prior to tissue degradation, during treatment of tissue degradation or following treatment for tissue degradation.

9. The system of claim 1, wherein the processor generates an image of the potential tissue degradation on the patient's body for use in treating the tissue prior to tissue deterioration.

10. The system of claim 1, wherein the electromagnetic detector comprises at least one of spectral imagers, digital sensors, analog sensors, photomultiplier tubes, bolometers or microbolometers, charge coupled device sensors, charge injection sensors, linear scan sensors, surface acoustic wave sensors, quartz crystal resonators, metal oxide sensors, dye-coated fiber optic sensors, dye-impregnated bead arrays, micromachined cantilever arrays, chemically-sensitive resistor or capacitor films, metal-oxide-semiconductor field effect transistors, infrared sensors, ultraviolet sensors, and bulk organic conducting polymeric sensors.

11. The system of claim 1, wherein the patient support comprises an array of chambers, wherein a pressure within each chamber can be varied individually or in groups.

12. The system of claim 1, wherein the tissue health is selected from bed sores, cancerous lesions, skin grafts, skin temperature, skin oxygenation, burns, skin trauma, skin diseases, autoinflammatory diseases, autoimmune diseases, infectious diseases, and combinations thereof.

13. An integrated system for patient treatment,
the system comprising: a patient support comprising one or more substrates; an electromagnetic detector positioned to detect one or more parameters of a patient's tissue health, wherein the detector measures tissue in contact with or adjacent to the patient support;
a light source that emits waves;
wherein the electromagnetic detector detects wave reflections from the patient's tissue, wherein the wave emissions and reflections are selected to traverse the one or more substrates positioned between the electromagnetic detector and the patient's tissue;
a processor connected to the detector that stores one or more parameters of the tissue's condition that are indicative of tissue health, wherein an indication of tissue health is used to change conditions at or about the site of tissue contact; and
one or more patient diagnostic and treatment devices connected to a network, wherein each of the devices can communicate to a network and exchange information with the network about the care of a patient; and
wherein the processor is accessible adjacent to the bed and connected to the network to integrate information obtained from the devices through the network with one or more additional sources of information databases, wherein the processor can communicate to one or more patient treatment devices and the processor either directly or via the network directs the one or more patient treatment devices to change the treatment of the patient.

14. The system of claim 13, further comprising a storage media in communication with the processor to store the patient's tissue health information and a display monitor in communication with the processor to display the patient's tissue health information.

15. The system of claim 13, wherein the processor is connected to one or more support repositioning devices that automatically move the patient if a change in tissue health is detected.

16. The system of claim 13, wherein portions of tissue that show a change in tissue health are marked with a fiducial for continued monitoring.

17. The system of claim 13, wherein the processor is connected to one or more devices at the patient support that heat, cool, increase, decrease humidity, systemic pharmaceuticals, increased oxygen delivery, decrease pressure, increase pressure of the tissue at or about a site in need of treatment.

18. The system of claim 13, wherein one of the one or more patient treatment devices comprise at least one of a ventilator; a vacuum hose; an intravenous pump; a catheter; a dialysis machine; a blood occlusion regulator; an oxygen administration device; an infusion unit; and a nitrous oxide administration device; a chemotherapy device; a radiotherapy device; an enteral feeding device; or a defibrillator.

19. The system of claim 13, wherein one of the patient diagnostic devices is at least one of an x-ray detector, hematology measuring device, a sphygmomanometer; a tonometer; an electroencephalograph; an impedance cardiography device; a carbon dioxide measuring device, a pulse oximeter; an electrocardiogram; a bispectral index; a scale; a pressure, flow and/or volume measurement device; a non-invasive blood pressure device; an invasive blood pressure device; a thermometer; a transcutaneous Doppler device; a transesophageal Doppler device; or a fluorescence activated cell sorter; a conductance meter or a hyperspectral imager.

20. The system of claim 13, wherein one of the patient diagnostic and treatment devices is a monitor for displaying a patient's condition.

21. The system of claim 13, wherein the tissue health is selected from bed sores, cancerous lesions, skin grafts, skin temperature, skin oxygenation, burns, skin trauma, skin diseases, autoinflammatory diseases, autoimmune diseases, infectious diseases, and combinations thereof.

* * * * *